(12) United States Patent
Dozortsev

(10) Patent No.: US 10,989,688 B2
(45) Date of Patent: Apr. 27, 2021

(54) TECHNIQUES FOR EXTENDING ELECTRODE SERVICEABILITY AND USEFUL LIFE IN VOLTAMETRIC DEVICE

(71) Applicant: AMS Trace Metals, Inc., Wilmington, DE (US)

(72) Inventor: Vladimir Dozortsev, Ridgewood, NJ (US)

(73) Assignee: AMS Trace Metals, Inc., Wilmington, DE (US)

( * ) Notice: Subject to any disclaimer, the term of this patent is extended or adjusted under 35 U.S.C. 154(b) by 211 days.

(21) Appl. No.: 16/277,927

(22) Filed: Feb. 15, 2019

(65) Prior Publication Data

US 2019/0257788 A1    Aug. 22, 2019

Related U.S. Application Data

(60) Provisional application No. 62/631,790, filed on Feb. 18, 2018.

(51) Int. Cl.
  *G01N 27/48*    (2006.01)
  *G01N 27/38*    (2006.01)
  (Continued)

(52) U.S. Cl.
  CPC .......... *G01N 27/48* (2013.01); *G01N 27/301* (2013.01); *G01N 27/38* (2013.01);
  (Continued)

(58) Field of Classification Search
  CPC .......... G01N 33/1813; G01N 35/092; G01N 27/301; G01N 27/444; G01N 27/38; G01N 33/208; G01N 35/0092; G01N 27/44
  See application file for complete search history.

(56) References Cited

U.S. PATENT DOCUMENTS

| 4,889,611 A * | 12/1989 | Blough, Jr. .......... G01N 27/403 204/411 |
| 2008/0017523 A1* | 1/2008 | Dietze .................... G01N 27/38 205/794.5 |

OTHER PUBLICATIONS

Yantasee et al., "Automated portable analyzer for lead(II) based on sequential flow injection and nanostructured electrochemical sensors," Talanta 68 (2005) 256-261 (Year: 2005).*

(Continued)

*Primary Examiner* — Alexander S Noguerola
(74) *Attorney, Agent, or Firm* — Marc P. Schuyler

(57) ABSTRACT

This disclosure provides techniques for extending useful life of a reference electrode, as well as a novel voltametric system and measurement cell design and related chemistries. An automated, repeatable-use system features a reference electrode that directly immerses a metallic conductor into an analyte, with electrolytes (e.g., chlorides) used for measurement being separately added and removed for each measurement cycles; the metallic conductor can optionally be left exposed to clean dry air in between measurements. In one implementation, the system can be restricted to application with specific analytes (e.g., ground water) that are known in advance to be free of substances that could degrade reference electrode use or lifetime. Cleaning solutions can optionally be used that would not be practical with conventional (insulated) reference electrode designs. In another embodiment, a measurement cell can be configured to receive separated electrode modules, permitting independent cleaning/removal of the working electrode (or other electrodes).

20 Claims, 9 Drawing Sheets

(51) Int. Cl.
| | |
|---|---|
| *G01N 27/403* | (2006.01) |
| *G01N 27/30* | (2006.01) |
| *G01N 35/00* | (2006.01) |
| G01N 27/34 | (2006.01) |
| G01N 33/208 | (2019.01) |
| G01N 33/18 | (2006.01) |

(52) U.S. Cl.
CPC ..... *G01N 27/4035* (2013.01); *G01N 35/0092* (2013.01); *G01N 27/34* (2013.01); *G01N 33/1813* (2013.01); *G01N 33/208* (2019.01)

(56) References Cited

OTHER PUBLICATIONS

Christopher Jesudason, "Broad Considerations Concerning Electrochemical Electrodes in Primarily Fluid Environments," Int. J. Mol. Sci. 2009, 10, 2203-2251 (Year: 2009).*

* cited by examiner

TECHNIQUES FOR EXTENDING ELECTRODE SERVICEABILITY AND USEFUL LIFE IN VOLTAMETRIC DEVICE

CROSS-REFERENCE TO RELATED APPLICATIONS

This application claims the benefit of U.S. Provisional Patent Application No. 62/631,790, filed on Feb. 18, 2018 on behalf of first-named inventor Vladimir Dozortsev for "Techniques for extending electrode serviceability and useful life in voltametric device;" the aforementioned patent application is hereby incorporated by reference.

BACKGROUND

Voltametric measurement methods are used for detection and measurement of various substances, particularly concentration levels of various metals in aqueous solution. A typical voltametric measurement system employs a measurement cell with a mechanism for ingress and egress of the aqueous solution under analysis and electrodes to measure current flow; metal concentration is determined based on this current flow. A typical configuration is a three electrode system, featuring a "working" electrode, a reference electrode and an "auxiliary" electrode. The resistivity of the aqueous solution under analysis can vary, and the reference electrode is used to provide a stabilized reference potential, so as normalize voltages and enable accurate measurement of current flow between the working electrode and the auxiliary electrode. These measurement techniques are applied to a wide range of fields, for example, to water metrology, to medial applications (e.g., to test a patient's blood) and, generally, to any situation where it is desired to monitor a fluid for presence and/or specific concentrations of a specific metal or specific metal form or compound.

In one class of these applications, it is desired to provide for remote, repeatable-use detection and measurement systems. For example, in one application, it is desired to intermittently sample a liquid to monitor for the presence and/or concentration of a specific metal as constituency of the liquid changes over time. An example of this application is the automated monitoring of a water supply (e.g., well water) for presence of a harmful material (such as lead, chromium, selenium, copper, arsenic, etc.); it is desired to have systems that on an ad-hoc or calendared basis "draw" samples from the water source and identify whether concentration of a specific is within acceptable limits. However, generally speaking, it is quite difficult to manufacture a reliable, automated, high-use-cycle voltametric measurement device for this purpose. Depending on application, the electrodes can become befuddled and must typically be frequently cleaned and/or replaced to provide for continued measurement accuracy; for example, the "working electrode" must typically be periodically buffed or polished to provide for continued use, and the reference electrode typically degrades after a few measurements and must be closely monitored and frequently replaced. In this latter regard, the reference electrode typically is embodied in an "insulated" design where a silver wire is encased within a hollow glass tube; the glass tube contains a potassium chloride solution and a porous interface to permit exchange of charge carriers produces during voltametric measurement. The potassium chloride (or other salt) solution is typically important, as it permits charge carrier exchange with the analyte, and provides for a stable reference electrode effective surface (e.g., of silver-chloride) during measurement. This conventional reference electrode design also provides a structural half-cell that helps insulate the reference electrode conductor (e.g., the silver wire) from interfering substances, particularly from organics, which might be present in the analyte during measurement and which might otherwise occlude the effective surface area of the reference electrode conductor. Unfortunately, over time, the porous membrane can still become befuddled (e.g., clogged or contaminated with substances from prior measurements), the potassium chloride solution can leak or dry out, and contaminants can leach into the potassium chloride solution (and/or onto the electrode); each of these types of degradation can interfere with proper reference electrode function. There are typically no cleaning methods that can reliably be used in such an analytical system to ensure high-use cycle electrode lifetime and, as a consequence, it is typically necessary to frequently replace the reference electrode; as this electrode is encased (insulated) within a glass tube, replacement is typically not easily performed in the field, and manufacturers typically provide a modular electrode system where the working electrode and the reference electrode are part of a larger (relatively expensive) assembly that is typically replaced as an integral unit. For example, in one system, these electrodes are mounted together by a single modular body, which is then sold as a replacement part (i.e., typically for hundreds to thousands of dollars).

What are needed are techniques for providing for enhanced electrode reliability and useful life in a measurement cell and voltametric measurement device, especially for field-based applications (e.g., such as automated monitoring of various liquids, including without limitation potable and non-potable water supplies). More specifically still, what are needed are techniques for enhancing reference electrode useful life and otherwise improving the ease of field-based maintenance. The present invention satisfies these needs and provides further, related advantages.

Figure 1:
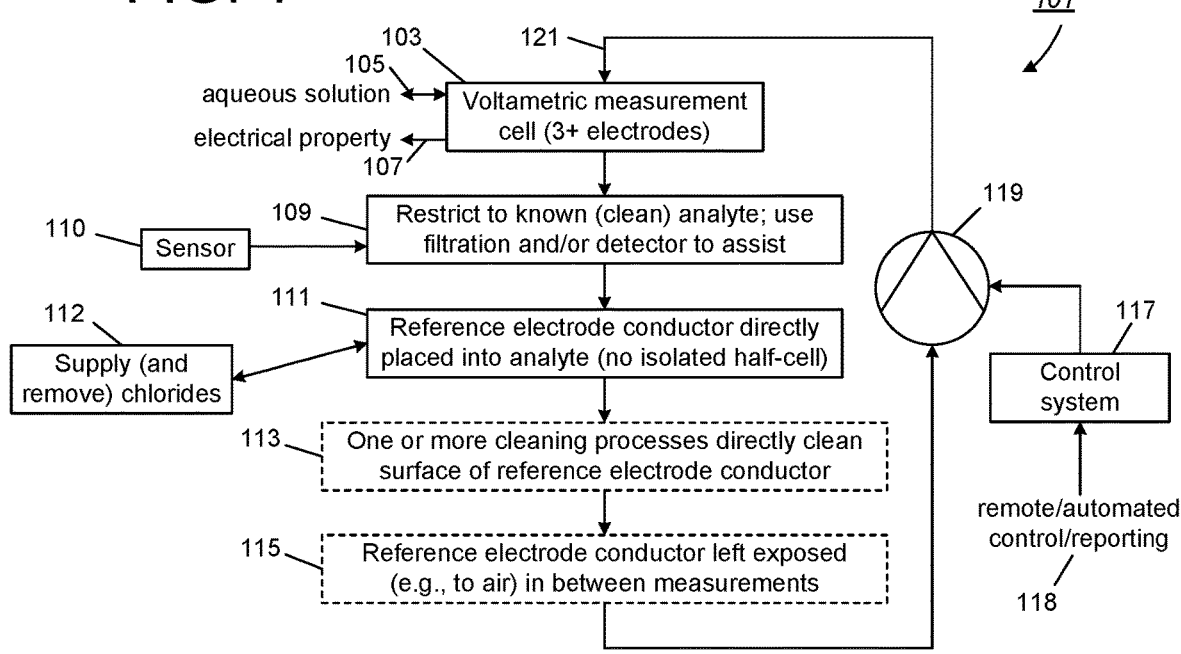
FIG. 1 provides a flow chart showing techniques for improved voltametric measurement that overcome some of the problems referenced earlier.

The subject matter defined by the enumerated claims may be better understood by referring to the following detailed description, which should be read in conjunction with the accompanying drawings. This description of one or more particular embodiments, set out below to enable one to build and use various implementations of the technology set forth by the claims, is not intended to limit the enumerated claims, but to exemplify their application. Without limiting the foregoing, this disclosure provides several different examples of techniques for improving voltametric measurement. The various techniques can be embodied in various forms, for example, in the form of application-specific techniques (e.g., water supply management, potable water management, field-based metal concentration measurement), in the form of a specific measurement cell and/or electrode configuration, and techniques for their maintenance and/or replacement, and in a voltametric measurement system; still further, and by way of example only, the novel techniques provided by this disclosure can be embodied as systems, devices and techniques for remote, automated measurement of specific analytes (e.g., arsenic, selenium or other metals) on a highly-automated basis. While specific examples are presented, the principles described herein may also be applied to other methods, devices, chemistries and systems as well.

DETAILED DESCRIPTION

This disclosure provides devices, systems, methods, chemistries and related techniques for improving useful life of a measurement cells and/or a reference electrode in a voltametric measurement system. More particularly, this disclosure provides techniques that can be applied to provide for facilitated electrode maintenance, easier replacement, and in-situ electrode and/or system cleaning; these techniques thereby enhance the convenience and serviceability of field-based analytical systems. These techniques are specifically advantageous for systems and chemistries adapted for in-line automated measurement of water supplies to measure levels of trace metals.

In one embodiment, these techniques can take the form of a measurement cell, voltametric measurement system and/or chemistry-specific measurement device adapted to the measurement of a metal (e.g., selenium or arsenic) in potable water, waste water, or another substance of generally-known chemical constituency. Optionally, a sensor can be used to detect presence of electrode-degrading substances such as organics in the water supply (e.g., where organics or other specific substances are greater than a threshold, such as $>=5.0$ parts-per-million, or "PPM"); alternatively, such a system can instead be limited in its application where the substance being measured (e.g., ground water) is presumed to be free of such undesired substances. By guaranteeing a relatively clean analyte, techniques presented herein effectively discard need for the conventional reference electrode design and instead utilize a substitute electrode/conductor structure (e.g., a silver or silver chloride wire which is directly exposed to the analyte of interest during the measurement process, that is, without a built-in glass tube, electrolyte or other conventional "half-cell" or "insulated" design). As but one non-limiting example, such a voltametric measurement cell and/or system can be limited to ground water applications (e.g., well water applications where the water is known to always be free of organics or other substances that might interfere with reference electrode operation). Other applications are also possible.

In a specific application, because the conventional reference electrode design is replaced by a conductor that is directly immersed in a measurement sample, the measurement specially process introduces chloride (or another electrolyte) to a measurement cell having this exposed conductor, thereby facilitating voltametric measurement; for example, in addition to introducing the measurement sample, a fluidic transfer mechanism can also introduce hydrochloric acid (or another source of chloride) to act as a buffer during the measurement process. This addition provides the electrolyte used for the measurement process, once again, obviating the need for a traditional "insulated" reference electrode structure. In one embodiment, these techniques are used for metal-specific detectors, such as for the detection of arsenic or selenium concentrations, where chlorides are specially introduced into the measurement process (e.g., for use in association with the reference electrode, to provide for a stable silver-chloride conductor during measurement and are then removed following measurement). Optionally, following measurement, the reference electrode is rinsed (e.g., with deionized water) or is otherwise cleaned to renew the electrode for an ensuing measurement cycle. Limiting the use of such a measurement cell, as described above as an optional process, helps ensure long electrode useful life by minimizing exposure to organics (and/or other substances) which can either react with or otherwise denigrate or obscure useful electrode surface area, and it also permits cleaning of the electrode(s) using chemicals that might be inconsistent with (e.g., degrade or leach into) the conventional "insulated" reference electrode design. In one embodiment, the voltametric system can employ a calibration process to sense shifts in electrode function and optionally gate the application of (chemical or ultrasonic) cleaning cycles or other forms of electrode servicing and/or replacement.

Note that with the techniques described above, it is not required that the reference electrode be handled so as to avoid dry-out between measurements. This is to say, it is not necessary to maintain a reference electrode in a chloride-based solution during the interval between voltametric measurements; it is therefore possible in some embodiments to leave the reference electrode exposed to dry air in between measurements. Clogging or cleaning of a porous membrane and contamination of a persistent electrolyte is also not a concern. Finally, as noted, because the porous membrane and build-in electrolyte of a conventional "insulated" reference electrode is not utilized, it also becomes possible to introduce cleaning solutions to the measurement cell (e.g., certain acids and/or fluorides) which might be incompatible with (e.g., damage or destroy) a conventional reference electrode structure. These and other advantages will be discussed below.

In a second embodiment, a set of measurement techniques can take advantage of the structures just introduced. For example, in one embodiment, voltametric measurement methods are applied to measure concentration of a metal of interest, for example, arsenic or selenium (or a specific form of these or other metals). A sample of a solution is intermittently drawn, for example, a known volume of water (e.g., 4.5 mL). Optionally, this sample can be first processed chemically or using heat or ultraviolet light, e.g., to convert metal in one form to another form more suitable for testing (e.g., selenium-6 to selenium-4). A source of chlorides is added to this sample, for example a specific volume and concentration of hydrochloric acid (e.g., 0.5 mL of 0.20 molar HCL for arsenic concentration measurements and 0.5 mL of 2.00 molar HCL for selenium concentration measurements). The solution is mixed within—or is introduced into—a measurement cell where that solution is directly exposed to working electrode, reference electrode and auxiliary electrode conductor surfaces, that is, without relying on the "insulated" structure typically featured by a conventional reference electrode design. A stripping voltametric process is then used, where metal is first plated onto the working electrode and then is stripped off, with current flow between the working and auxiliary electrodes being measured and with the reference electrode providing a stable reference potential (e.g., using a silver-chloride effective surface). The voltametric system produces measurements as a function of applied potential difference and time. Solution is then drained from the measurement cell, which is then rinsed (e.g., with deionized water or another neutral substance) to renew it for an ensuing measurement cycle. Optionally, one or more cleaning processes can then be applied, for example, which directly clean a surface of the conductor for the reference electrode; a calibration test (e.g., a spike test) can then optionally be used to test for acceptable health of the various electrodes (including the reference electrode). For example, one or more cleaning solutions and/or rinse cycles can be used without fear that the cleaning solution will corrupt a measurement electrolyte or porous membrane. A variation of this second embodiment can be implemented as a method of cleaning a voltametric measurement device or a measurement cell of a voltametric measurement device; as noted, the method can include removing a saline or other buffer solution from the presence of a reference electrode (e.g., silver or silver chloride wire), leaving an exposed conductor surface. This surface can then be subject to ultrasonic cleaning or chemical cleaning with an acid or fluoride-based substance, which would not typically be possible with a conventional reference electrode design. In a further variation, such cleaning processes can be applied to another electrode (such as the working electrode) in the presence of the reference electrode. Because a "half-cell-less" design is used, the working electrode is robust to these processes (which would conventionally not be the case for a working electrode premised on a porous membrane, as alluded to above).

A third embodiment provides a measurement cell and/or measurement cell module which facilitates cleaning and/or electrode replacement. For example, instead of mounting three electrodes within a single replaceable module, as is sometimes conventionally done, techniques disclosed herein provide for an electrode module dedicated to the working electrode. In one version of this embodiment, the auxiliary electrode (e.g., a platinum wire) and the reference electrode (e.g., a silver wire) have a common or dedicated connection methodologies (e.g., a dedicated module, for example, made out of plastic or another neutral substance) while the working electrode can be separately and independently replaced, e.g., via an independent replacement module; such a structure facilitates independent removal of (and servicing of) the working electrode and, conversely, it does not require replacement of the working electrode simply because a conventional reference electrode structure must be replaced. In a second version, the working electrode can be positioned within a measurement cell so as to be placed in opposition to an ultrasound emitter, which is configured to apply ultrasonic techniques to the working electrode (e.g., notwithstanding presence of the reference electrode), further improving in-field and/or remote, automated servicing of the working electrode. This is to say, techniques introduced herein optionally permit the use of cleaning techniques or solutions for the reference electrode, as well as the other electrodes (e.g., the working electrode) in a manner that is not limited by the presence of a conventional "insulated" reference electrode design. The use of in-situ techniques for cleaning or renewal, in turn, reduces the need and/or frequency with which electrodes must be manually removed for special servicing or replacement, enhancing the field-based, automated applications referenced earlier.

These and other advantages will become apparent from the discussion which follows.

This disclosure will roughly be organized as follows: (1) FIGS. 1-2 will be used to provide an introduction of techniques for improving electrode lifetime and serviceability, including voltametric measurement techniques, electrode configurations, use of a special measurement cell, and other design features suitable for the purposes referenced earlier; (2) FIGS. 3A-3D will be used to introduce more specific techniques, and to discuss certain specific measurement cell designs; (3) FIGS. 4-5B will be used to discuss fluidics control associated with these techniques, as well as chemistries and chemical processes suitable for measurement of specific metals; (4) FIG. 6 will be used to discuss automated sample extraction; and finally, (5) FIGS. 7-9 will be used to discuss electronic control, especially from a networking standpoint.

Prior to proceeding to detailed embodiments, it would be helpful to first introduce certain terms used herein.

Specifically contemplated implementations can include an apparatus comprising instructions stored on non-transitory machine-readable media. Such instructions (or "instructional logic") can be written or designed in a manner that has certain structure (architectural features) such that, when the instructions are ultimately executed, they cause the one or more general purpose machines (e.g., a processor, computer or other machine) each to behave as a special purpose machine, having structure that necessarily performs described tasks on input operands in dependence on the instructions, to take specific actions and/or otherwise produce specific outputs. "Non-transitory" machine-readable or processor-accessible "media" or "storage" as used herein means any tangible (i.e., physical) storage media irrespective of the technology used to store data on that media, e.g., including without limitation, random access memory, hard disk memory, optical memory, a floppy disk, a CD, a solid state drive (SSD), server storage, volatile memory, non-volatile memory, and other tangible mechanisms where instructions may subsequently be retrieved by a machine. The media or storage can be in standalone form (e.g., a program disk or solid state device) or embodied as part of a larger mechanism, for example, a laptop computer, portable device, server, network, printer, or other set of one or more devices. The instructions can be implemented in different formats, for example, as metadata that when called is effective to invoke a certain action, as Java code or scripting, as code written in a specific programming language (e.g., as C++ code), as a processor-specific instruction set, or in some other form; the instructions can also be executed by the same processor or different processors or processor cores, depending on embodiment. Throughout this disclosure, various processes will be described, any of which can generally be implemented as instructions stored on non-transitory machine-readable media. Also depending on implementation, the instructions can be executed by a single computer and, in other cases, can be stored and/or executed on a distributed basis, e.g., using one or more servers, web clients, or application-specific devices. Each function mentioned in reference to the various FIGS. herein can be implemented as part of a combined program or as a stand-alone module, either stored together on a single media expression (e.g., single floppy disk) or on multiple, separate storage devices; as used herein, the term "module" refers to a device comprising hardware logic (mechanical structures and/or elements) and/or instructional logic whose components are not shared with other modules or circuitry. For example, a "sensor module" would include a sensor and one or more other components such as a housing, conduits, electronic leads, connection means and so forth which are dedicated to that module (and where a separate module would have its own dedicated components); similarly, a "first module" to perform a first specific function and a "second module" to perform a second specific function, when used in the context of instructions (e.g., computer code) refer to mutually-exclusive code sets. When used in the context of mechanical or electromechanical structures (e.g., an "encryption module") the term "module" refers to components which might also include circuitry, other forms of hardware (e.g., optical or electronic components), and/or software. In all cases, the term "module" is used to refer to a specific structure for performing a function or operation that would be understood by one of ordinary skill in the art to which the subject matter pertains as a conventional structure used in the specific art (e.g., a software module or hardware module), and not as a generic placeholder or "means" for "any structure whatsoever" (e.g., "a team of oxen") for performing a recited function. "Electronic" when used to refer to a method of communication can also include audible, optical or other communication functions, e.g., electronic transmission can encompass optical transmission of information (e.g., via an imaged, 2D bar code), which is digitized by a camera or sensor array, converted to an electronic digital signal, and then exchanged electronically. "Mechanism" as referred to herein, does not represent a nonce or placeholder, but rather, refers to a structure comprising a set of mechanical elements, at least one of which is to be actuated to some type of motion or physical action, optionally under electronic or mechanical control; it may also include other structures, e.g., electrical, mechanical, fluidic, optical, etc., for supporting the associated actuation. As a non-limiting example of this, a "sample extraction mechanism" includes elements for drawing samples, at least one of which is actuated to motion; a sample extraction mechanism can include a pump or motion-controlled syringe, for example, which performs some type of motion, or a valve (which opens and therefore performs some type of motion or physical action) to draw samples for use as analytes in the measurement process. Throughout this disclosure, various processes discussed herein can be optionally implemented as "logic" (e.g., as hardware or instructional logic configured to perform a particular function, or as a combination of these things, depending on embodiment or specific design).

Also, references in this disclosure will also be made to various substances, especially metals. Unless otherwise noted, references to such substances should be understood to encompass references to other forms of or compounds involving the same substance. As a non-limiting example of this, reference to a metal (such as arsenic or selenium) should generally be understood to refer to compounds based on these metals, and indeed, to substances which include such metal and/or any of its forms, ions, compounds, allotropes, isotopes, oxides, valences, and so forth.

As used herein, "directly" immersed, or "direct" when referring to contact of an electrode with sample fluid means that an electrode surface directly contacts the fluid being measured, i.e., as contrasted with an "insulated" or "indirect" electrode design, which permits charge migration without direct contact between the electrode surface such as through a buffer solution and porous membrane as referenced earlier. As used herein, the term "preservative" refers to a fluid in which an electrode (such as a reference electrode) is stored when not in active measurement use; this fluid can include a liquid, for example, deionized water or a saline solution, and in some embodiments, it can also include clean dry air ("CDA"). Finally, the term "calendared" when referring to an act or sample extraction refers to a scheduled act, for example, drawing a sample at a prearranged time (e.g., "hourly").

Various other terms will be defined below, or used in a manner apparent from context.

FIG. 1 shows some techniques for improved voltametric measurement that overcome some of the problems referenced earlier. These techniques involve the use of a voltametric system 101 having one or more improved components and/or processes. In the depicted example, the system 101 uses a voltametric measurement cell 103 having three electrodes, including a working electrode, an auxiliary electrode and a reference electrode (not individually shown in the FIG.), as well as ingress/egress 105 for an analyte (an aqueous solution that is to be measured or monitored). The measurement cell and its electrodes are used to measure an electrical property 107, for example, a current flow, potential difference, resistivity, conductivity or other electrical property. In this particular example, the voltametric system can be a stripping voltametric system, e.g., which typically operates using potential different and/or current to (a) in a first phase, plate the working electrode with a specific substance from the analyte, generally a specific metal or metal compound, and (b) in a second phase, strip that metal off of the working electrode while measuring the electrical property (e.g., current flow versus time and/or applied voltage). The disclosed techniques are not limited to stripping voltammetry, and can be applied to other forms of voltammetry.

Conventionally, an "insulated" design would be used for the reference electrode, in large part to provide for proper function of the reference electrode (i.e., isolating it from the contaminants such as certain organics, which could hinder its primary function of providing a reliable reference potential). As indicated by numerals 109 and 111, however, in the depicted embodiment, such a design is not used for the reference electrode; rather, steps are taken to ensure that the voltametric system 101 and/or the measurement cell 103 are exposed to only relatively "clean" analytes, for example, which do not contain these organics or other substances that could interfere with reference electrode function. For example, in one contemplated application (e.g., automated measurement of certain potable water supplies, such as ground water), which generally is well-filtered but can have a high mineral and/or metal content, the water supply is indeed "clean" and the voltametric system 101 can be readily applied without special filtering, treatment and/or switching techniques. In another implementation, an optional sensor 110 can be used to test the sample for undesired particulate (e.g., excessive organics) upstream of the voltametric measurement system, with measurement system selection being made in response to such a test; in still another embodiment, such testing can be used to selectively filter the sample so that it is then amenable for voltametric measurement. Whichever process is used, this the depicted method facilitates the use of a reference electrode having a conductor that is directly immersed in the analyte of interest, that is, without using reference electrode conductor isolation, as indicated by numeral 111. Per numeral 112, in such an embodiment, (that is, in an embodiment where no chlorides are inherently part of the reference electrode structure), a buffer solution containing chloride or an equivalent can be specially added as part of the measurement process (and then removed following measurement). To take another example, one contemplated application is to the measurement of arsenic and/or selenium in a water supply; a buffer solution containing chlorides is directly mixed into the water sample, in order to supply chlorides to the reference electrode, e.g., to form silver-chloride and thereby provide a stable reference electrode structure during measurement. As indicated further by numeral 112, as part of the process, once the measurement cycle is finished, this mixture (including the added chlorides) is then removed from the measurement cell and electrode conductors, i.e., leaving them directly exposed to air (or another preservative). Because chlorides (or an equivalent) are then later added with each measurement cycle, this then provides a stable state for the electrodes in between measurement. Optionally, as indicated by numeral 113, one or more cleaning processes can also then be introduced to the measurement cell. For example, as will be discussed below, rinses, chemical processes and/or ultrasound can be used to renew the measurement cell for an ensuing process. In one embodiment, deionized water is simply used to rinse the measurement cell, which is then left exposed to dry air in between measurements, per numeral 115. In another embodiment, chemicals such as acids can be used to clean the electrodes so as to remove any surfactants, oxides or other inhibitors and thereby provide for continued electrode function; as but one example, many substances (e.g., fluoride-based acids) would typically not be used with a conventional measurement cell (e.g., because they are highly corrosive to the conventional reference electrode design, and in particular glass and ceramic); however, because an "insulated" reference electrode is not used by present designs, it becomes possible to use chemical cleaners to a much greater degree than otherwise possible (i.e., subject to compatibility with other system materials and chemistries). In yet another embodiment, separating the reference electrode from the working electrode and instantiating the reference electrode as a simple wire conductor permits the use of other types of automated cleaning processes, for example, ultrasound as a means of efficiently cleaning the working electrode in-situ. The ability to use a measurement cell which (a) is not subject to electrode dry out, e.g., it does not use a half-cell design with built-in electrolyte, and (b) is compatible with chemical and ultrasonic cleaning processes, should all be understood as promoting high-use-cycle measurement cells, sensors and voltametric systems and otherwise facilitating (1) automated, remote measurement systems, (2) enhanced electrode maintenance, particularly in field applications, (3) long device and system lifetimes, and (4) reduced costs in required maintenance and/or component replacement.

FIG. 1 shows a few other elements that should be understood as contributing to these benefits. First, as represented by numeral 117, the entire system and/or process can be managed by a control system (typically, using one or more processors, for example, local digital electronics, memory for storing operands and results, and network communications electronics, as well as a remote computer that provides for remote control and/or reporting, as indicated by numeral 118. This control system controls, in addition to the various electrodes, a fluidics transport mechanism 119 (typically rooted in an electric syringe or a pump, and suitable tubing and valving, used to provide fluidic ingress and egress, as discussed throughout this document). Finally, as indicated by numeral 121, one function of these systems is to renew the measurement cell 103, i.e., such that it is ready for another measurement (e.g., automatically, on a calendared or ad-hoc basis). These various features and their advantages will be further discussed below.

Figure 2:
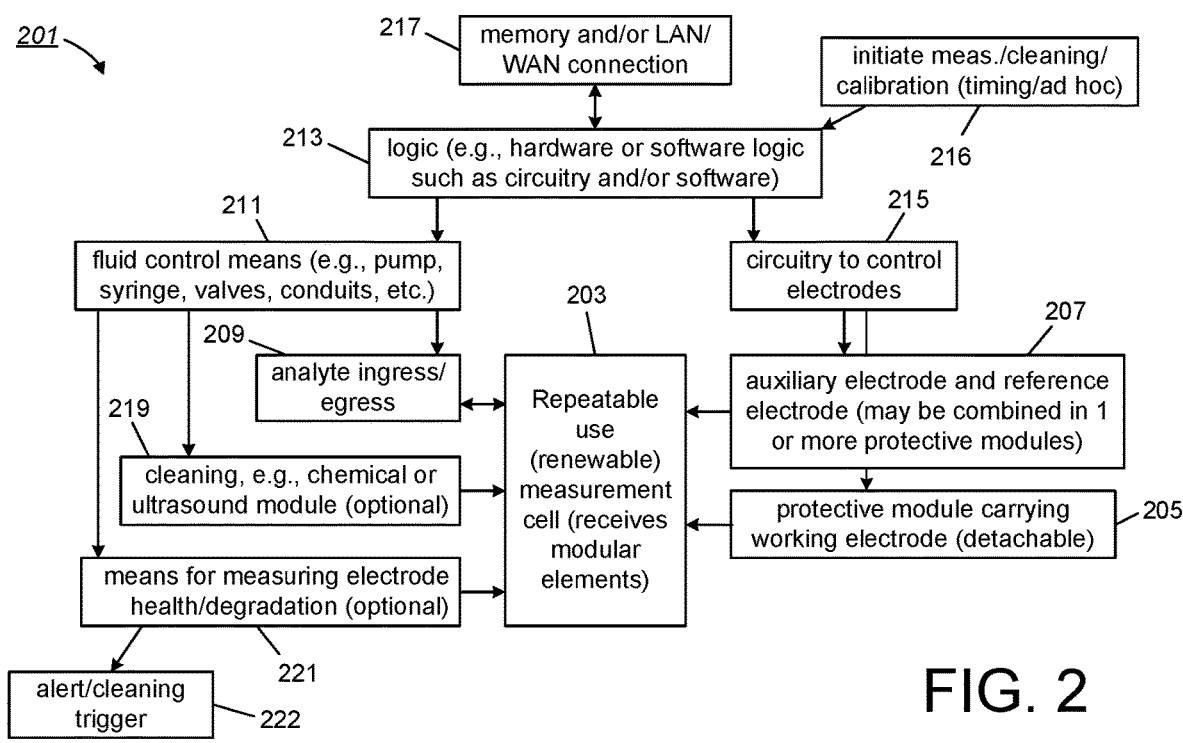
FIG. 2 is a block diagram that shows control and measurement functions associated with one non-limiting example of a field-based, repeatable-use voltametric measurement system.

FIG. 2 is a block diagram that shows control and measurement functions associated with one non-limiting example of a field-based, repeatable-use voltametric measurement system, generally represented by numeral 201. A central component of this system is a repeatable-use measurement cell 203 that is based on a "bare conductor" reference electrode design, as was introduced above. This measurement cell is a renewable cell, meaning that it can automatically be cycled, e.g., on a remote basis, to perform measurements many times, with the measurement cell being rinsed, cleaned, cleared, or otherwise prepared in between measurements for an ensuing measurement cycle. As also indicated by the FIG., the measurement cell can also optionally be based on modular elements, for example, a module that houses the working electrode in a manner independent from the other electrodes 205, thereby enabling the working electrode to be independently removed and serviced (or otherwise exchanged). For example, such an electrode module can comprise a plastic housing, the working electrode itself (i.e., in a manner mounted by the housing), a means for ingress/egress of electronic leads for the electrode and, optionally, a connection mechanism to matingly-attach-and-detach the electrode module to/from the measurement cell. This then permits the working electrode to be replaced as an individual unit in the field, or otherwise removed, mechanically buffed (e.g., for special, infrequent cleaning or maintenance), and reinserted for renewed use. As noted by numeral 207, the measurement cell also features an auxiliary electrode and reference electrode (which may similarly be housed in one or more electrode modules, e.g., either a combined module which mounts both of these electrodes, or in respective modules that may be independently detached from/attached to the measurement cell 203; in practice, each of these electrodes places a wire (platinum in the case of the auxiliary electrode, and silver or silver-chloride in the case of the reference electrode) into immersive contact with a measurement sample within the measurement cell 203. Per numeral 209, the measurement cell also features one or more channels for sample ingress and egress and also for overfill protection and/or venting.

Fluidics control in such a system is typically managed by a fluidics control means (e.g., a pump or motion-controlled syringe, and associated valves and conduits that transport fluids between various supplies, the measurement cell, and drains as appropriate), as indicated by numeral 211. As will be discussed further below, in one exemplary implementation, this means can optionally include a rotary selector which provides the capability of switching any one of a number of fluids for supply to the measurement cell, potentially including samples, one or more buffers (e.g., providing for selective addition of a controlled amount of electrolytes/chlorides, potentially at multiple, respective concentrations depending on whether the system is configured to measure multiple, different analytes at different times), a rinse solution (e.g., deionized water), standards for purposes of testing and calibration, supply of spent fluids to a waste receptacle, a preservative, and one or more cleaning solutions), and so forth. In one embodiment, a filter or switch can also optionally be used to restrict application of the system 201/measurement cell 203 (and its electrodes) to relatively "clean" liquids; that is, for example, the rotary selector in one embodiment can feed samples to a filter or testing device, with either filtered solution being used as the measurement sample, or with further use of the measurement sample made contingent on "approval" of the sample based on an electronic output of the testing device. For example, the system can optionally include a sensor that detects the presence of excessive organics, with the specific sample being discarded (or switched to a different system or different measurement cell) if presence of this threshold condition is violated.

The sequencing of fluidics movement (e.g., control over valving, use of a rotary selector if present, access to the various liquids and their movement through the system) is managed by control logic 213, for example, a combination of hardware logic, such a digital controller such as a microprocessor, FPGA, or other hardware logic, with software logic. This logic also controls the electrodes, as implied by numeral 215, by controlling operation of electronic switches, charge pumps, voltage levels, and any associated sensors, and otherwise initiating measurements/cleaning/calibration on a timed (calendared) or ad-hoc basis 216. This logic also monitors fluid level sensors (e.g., associated with the measurement cell or a motion-controlled syringe, or otherwise with the fluidics) and other components of the system, for example, exercising control over valves and sensors used otherwise by the system. As noted earlier, the system can also use a filter or fluid-switching device that optionally helps regulate which samples the measurement cell is exposed to, and the control logic 213 can also exercise control over these components or reactions to outputs of these components. Finally, per numeral 217, the control logic 213 can also interact with memory and/or network connections (e.g., local area network or "LAN" connections, or wide area network or "WAN" connections) as appropriate; for example, the control logic 213 can perform calculations and store either concentrations and/or raw measurement data locally in memory, or report them "automatically" to a remote computer, server or database (e.g., via the Internet).

FIG. 2 also references that the subject system 201/measurement cell 203 can also optionally provide for cleaning options 219 and means for measuring electrode health and/or degradation, 221. That is, as referenced by logic block 219, the system can use (in addition to deionized water, as discussed above), chemicals and/or ultrasound to clean one or more of the three electrodes. In one embodiment, as discussed earlier, chemicals can be used to strip off any unwanted contaminants or oxides which could obscure or otherwise interfere with proper electrode function; selection of suitable cleaners or cleaning mechanisms will depend on electrode materials, any reactions triggered by the analyte and/or its associated chemistries, and presence of any contaminants such as unwanted organics or other substances in the sample; selection of cleaner/cleaning mechanism suitable to the application may be made by one having ordinary skill in the art, depending on these factors and on specific application. In one embodiment, as noted earlier, because a conventional glass/ceramic working electrode design is not used in the depicted measurement cell, relatively "harsh" cleaners (that could never be used as a practical matter with the conventional electrode design) can potentially be used, enabling a much greater degree of in-situ, automated electrode cleaning than was previously practical. As also noted by logic block 219, in another embodiment, another module may be received by the measurement cell to provide for ultrasonic cleaning; for example, such a module can comprise a housing that matingly-attaches-to-and-detaches-from the measurement cell so as to provide a fluidic seal and that positions an ultrasound emitter in close proximity to one or more of the exposed electrodes (e.g., directed at the surface of the working electrode, so as to deliver ultrasonic energy efficiently over the entire electrode surface). Once again, the control logic 213 can control operation over such activities, including initiation and control over ultrasonic cleaning and any associated rinse or other chemical processes. The control logic 213 also provides one element of the means for (automatically) measuring electrode health/degradation 221, e.g., periodically or intermittently, by monitoring electrode outputs (e.g., current levels) relative to expected levels; this can be performed using a periodic calibration such as a spike test or through detection of aberrant electrode readings/behaviors, or other mechanisms, and by automatically initiating electrode cleaning processes or the sending of an alert to a human operator (e.g., locally or remotely via LAN/WAN) to indicate that an electrode should be replaced 222.

As noted earlier, the techniques described herein also provide a novel measurement cell for voltametric applications, which facilitate use on an optional basis of the chemistries, modules, and electrode configurations, as discussed elsewhere herein. FIGS. 3A-3D are used to discuss specific embodiments of such a measurement cell. It should be understood that use of such a measurement cell is not required for implementation or practice of the chemistries and/or measurement processes and/or electrode configurations, as discussed herein; conversely, use of these chemistries/measurement processes/electrode configurations is not required for implementation of the measurement cell designs depicted in these FIGS.

Figure 3A:
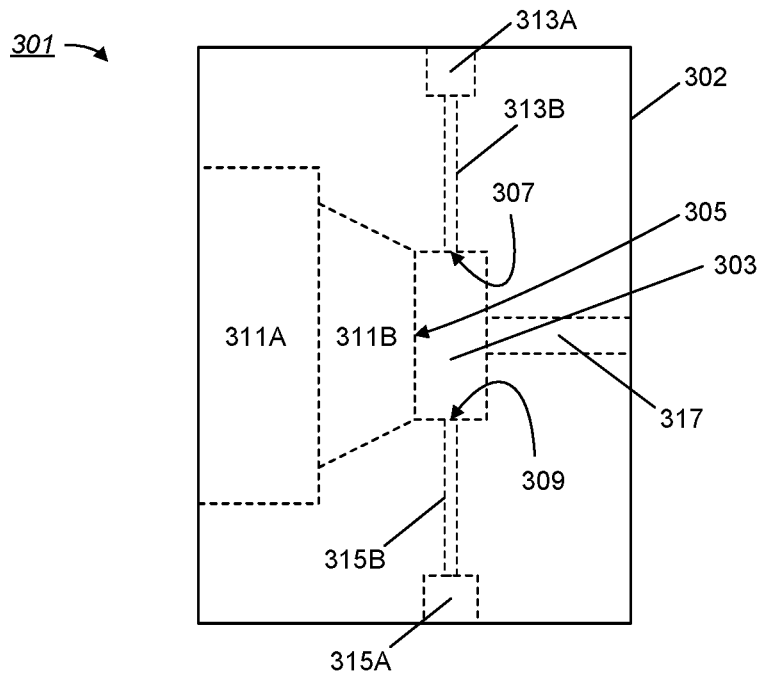
FIG. 3A shows a cross-section of a specific measurement cell design that implements some of the techniques discussed herein.

FIG. 3A provides a cross-sectional representation of a specific measurement cell 301 that implements some of the techniques discussed herein. The depicted measurement cell is effectively a cylindrical, non-reactive plastic block 302 having cavities as represented by dashed lines. These cavities can be formed with a precision drill, and otherwise with mechanisms for creating threading within the cavities so as to receive various individual modules, as will be described below. Numeral 303 references a fluidic measurement chamber that will receive liquid samples, and that directly immerses the exposed conductors of the three electrodes in the liquid samples. The measurement chamber 303 is suitably sized for the volume of sample to be processed in any given measurement cycle; for example, several applications discussed below perform measurements using approximately 5.00 milliliters (mL) of liquid, including sample, buffer and any required reagents (as appropriate). Numeral 305 designates a position where the surface of the working electrode will be exposed to samples, while numerals 307 and 309 respectively designate the positions of surfaces for the auxiliary electrode and reference electrode; as should be appreciated given the measurement cell volume discussed above, the depicted design positions the various electrode surfaces in very close proximity to each other (e.g., within 1-2 centimeters or less in some embodiments). These various electrodes are not depicted in the figure, but will be "screwed in" to the depicted block 302 during assembly. Numeral 311A designates a cavity that will receive a thread of a locking nut that will hold a module for the working electrode into place, while numeral 311B designates a cavity that will matingly-engage a housing of the working electrode module, i.e., canted surfaces of this cavity are matched to snugly match a housing for the working electrode module, so as to provide a fluidic seal. Similarly, numerals 313A and 313B respectively designate chambers that will receive a module for the auxiliary electrode, with chamber 313A providing a threaded recess which permits this module to be "screwed in" to block 302, and chamber 313B providing a cavity that will receive a sleeve that positions the auxiliary electrode so that the surface of its conductor is directly immersed in the measurement sample at position 307. Numerals 315A and 315B respectively designate chambers that will receive a module for the reference electrode, with chamber 315A providing a threaded recess which permits this module to be "screwed in" to block 302, and chamber 315B providing a cavity that will receive a sleeve that positions the reference electrode so that the surface of its conductor is immersed in the measurement sample at position 309. Finally, numeral 317 defines a channel for liquid ingress/egress (e.g., with selective supply and removal of samples, buffers, cleaning solutions, rinses, standards and so forth, being controlled under the auspices of control logic and fluidic control means, as discussed earlier). This channel can also partly supply means for overfill protection, as introduced earlier.

Figure 3B:
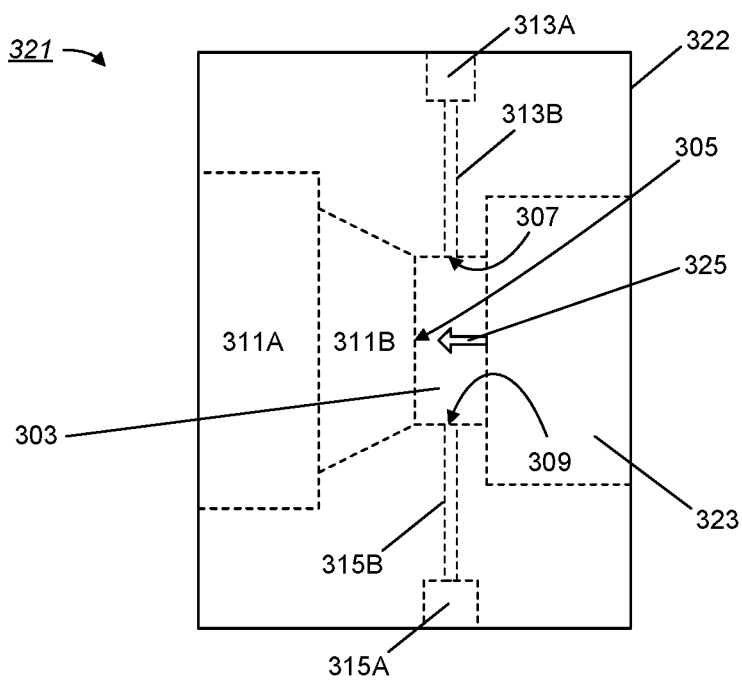
FIG. 3B shows a cross-section of another specific measurement cell design that implements some of the techniques discussed herein.

FIG. 3B shows a cross-section 321 of another specific measurement cell which implements some of the techniques discussed herein. In this FIG., numerals which are also referenced in FIG. 3A also refer to the same elements in this design. This measurement cell 321, however, features a plastic block 322 with a larger rear cavity 323; this cavity 323 is adapted to receive an ultrasound module, i.e., so as to provide a fluidic seal between this module and the block 322, and so as to position a relatively large ultrasound emitter surface in very close proximity to the working electrode (and, optionally, the other electrodes). In this depicted embodiment, ultrasound is directed from the emitter surface (not shown in the FIG.) in the general direction of arrow 325, so as to provide ultrasound over the entire conductive surface of the working electrode (i.e., at position 305). Again, the measurement cell volumes discussed above permit these components to be placed in very close proximity, in some embodiments, within ½ to 1 centimeter, facilitating the efficiently of ultrasonic cleaning. This cleaning can be initiated by the control logic (as discussed earlier), optionally in concert with a rinse or application of cleaning chemicals. As should be appreciated, this design also reduces the frequency with which the working electrode must be removed and serviced, e.g., in-situ "automatic" cleaning lessens the need for and frequency for manual/mechanical buffing, and permits selective removal of the working electrode module and/or the ultrasound module without need to remove/replace the other electrodes and/or their modules. That is, the electrodes can be periodically cleaned and/or serviced to a large extent without needing to disassembly the measurement cell or remove any of its components and, to the extent that disassembly is required, individual modules for the respective electrodes permit their replacement without needing to completely disassemble the measurement cell or replace all electrodes as a unit. Note that in such a configuration, fluidics ingress and egress can be provided by a different supply path than was depicted in FIG. 3A (e.g., from another radial conduit, such as designated by numerals 313A or 315A, not shown in this FIG., but extending into and out of the drawing page). Other configurations are also possible.

Figure 3C:
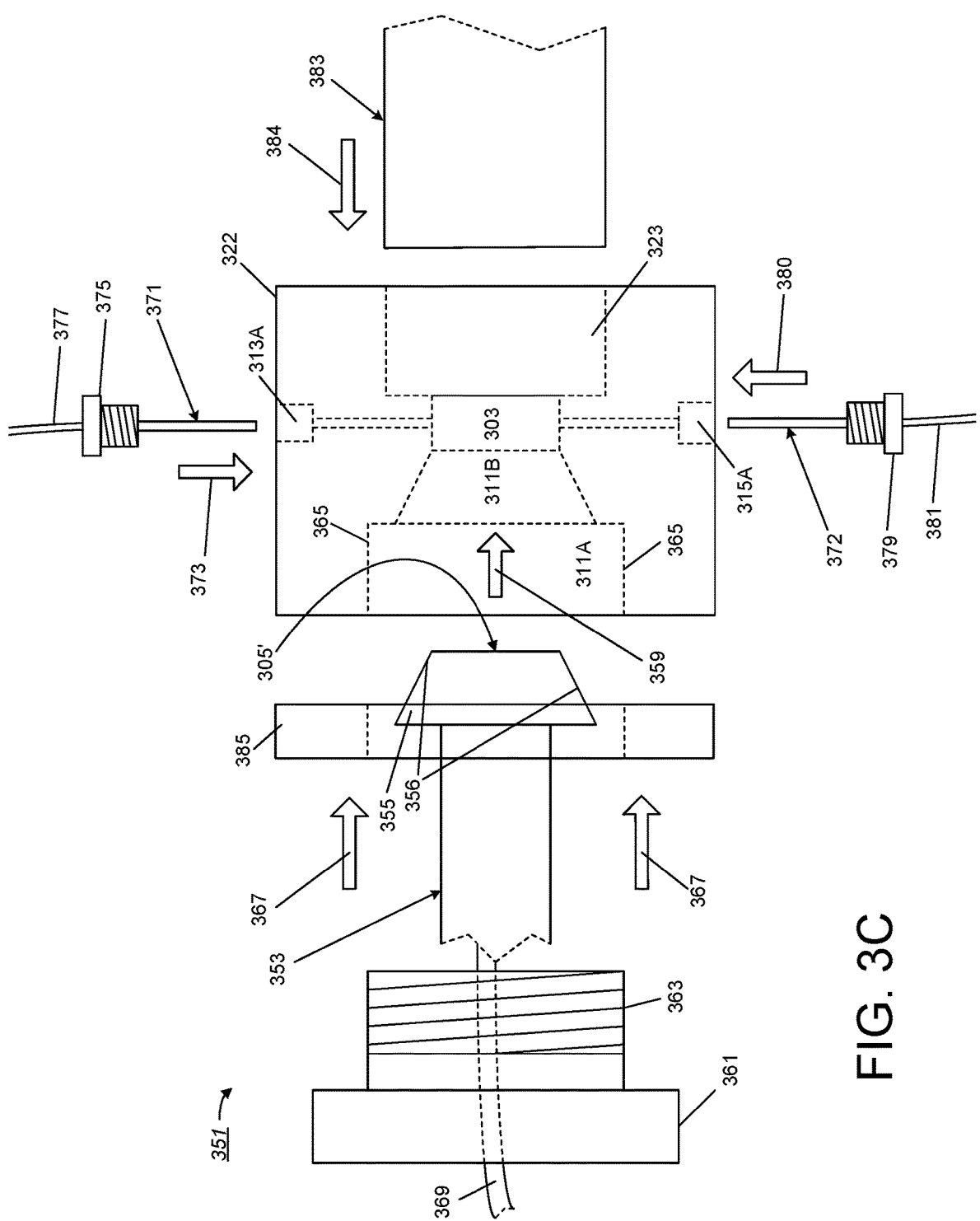
FIG. 3C shows a cross-section showing integration of various other components with the specific measurement cell design introduced by FIG. 3A or 3B.

FIG. 3C is a cross-sectional view 351 showing integration of various other components with the specific measurement cell design introduced by FIG. 3A or 3B. That is, this FIG. shows use of the plastic block 322 from FIG. 3B, but it should be understood that the plastic block 302 from FIG. 3A can instead be used. Once again, numbers referred to previously refer to the same design elements (e.g., from FIG. 3B).

A first component to be connected to the plastic block 322 is the working electrode module, designated by numeral 353. This module features a "mushroom-shaped" plastic housing having a head 355 with canted surfaces 356 which are adapted to interface with and seal to the lateral walls of cavity 311B. The working electrode is inserted as indicated by arrow 359 in order to make this contact and to place a surface of the working electrode, 305', into immersive contact with each measurement sample. The working electrode module is held in place by a locking nut 361, which provides a cylindrical threaded body whose threads engage reciprocal threads 365 on lateral walls of cavity 311A, with the locking nut 361 being tightened to urge the working electrode module toward plastic block 322 in the direction of arrows 367 and, in so doing, snugly hold the working electrode module in place. Numeral 369 refers to an electronic lead (e.g., insulated wire) that connects the electrode with associated electronics.

Second and third components adapted for insertion into block 322 include the auxiliary electrode module 371 and the reference electrode module 372. The auxiliary electrode module 371 is inserted into the measurement cell block 322 in the direction indicated by arrow 373, e.g., with a threaded base 375 being screwed into (reciprocal threads of) cavity 313A, and providing for egress of leads or wires 377 which conductively couple the electrode with supporting electronics. Similarly, the reference electrode module 372 is inserted into the measurement cell block 322 in the direction indicated by arrow 380, e.g., with a threaded base 379 being screwed into (reciprocal threads of) cavity 315A, and providing for egress of leads or wires 381, which again conductively couple the electrode with supporting electronics. The reference electrode can optionally be based on a "half-cell-less" design that directly immerses an electrode conductor surface directly into the measurement sample; as discussed earlier, this sample either contains or has injected into it chlorides, so as to provide for a suitable reference electrode effective surface during the measurement process (e.g., a silver-chloride effective surface). Although not shown in this FIG., additional cavities (e.g., threaded cavities) can also be used to provide fluid ingress/egress channels, as discussed previously. Note that FIG. 3C also shows an ultrasound module 383 which is inserted along direction 384 into the measurement cell block 322, i.e., for mating contact with cavity 323. Any suitable connection methodology may be used to ensure fluidic seal between the ultrasound module and measurement chamber 303. Note also that FIG. 3C shows a mounting bracket 385 which is used to mount the measurement cell to a housing of a voltametric system (this will be further discussed below in connection with FIG. 3D). In one embodiment, the measurement cell block (e.g., 302 from FIG. 3A or 322 from FIG. 3B) is made of clear plastic, i.e., so as to permit visual inspection of the state of the surface of the measurement cell and the state of the various electrode surfaces without need to disassemble the measurement cell or remove its various modules. In one optional embodiment, a visual sensor (e.g., a camera or light detector) can be used to monitor such a measurement cell block for internal buildup of undesired surface particulate, e.g., with cleaning cycles and/or operator alerts being responsively triggered (i.e., as was introduced in connection with the discussion of FIG. 2, above).

Figure 3D:
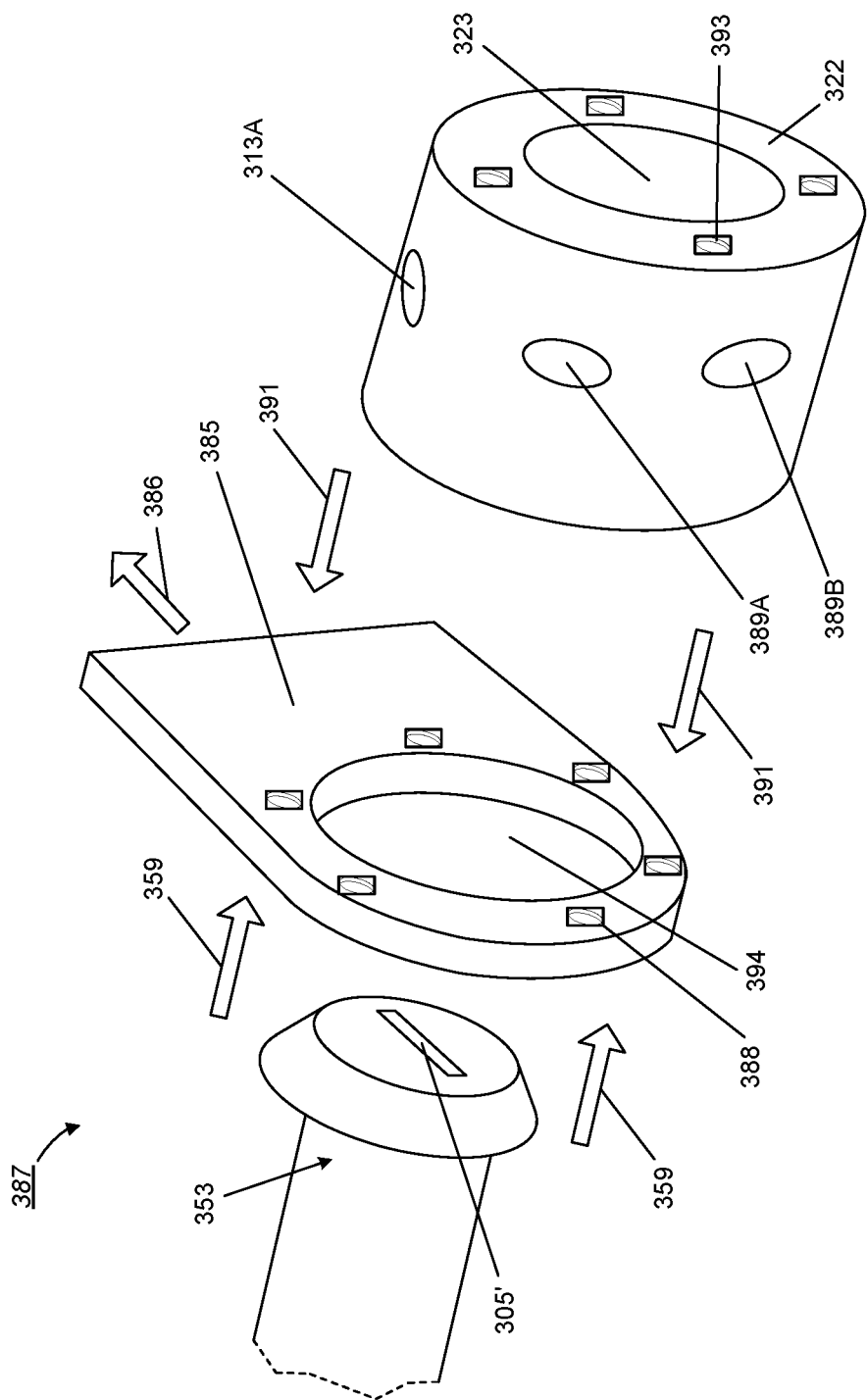
FIG. 3D is a perspective view showing further integration of various other components with the specific measurement cell design introduced by FIG. 3A or 3B.

FIG. 3D is a perspective view 387 showing further integration of components with the specific measurement cell design introduced by FIG. 3A or 3B. As noted above, a mounting arm 385 is used to mount the measurement cell relative to a housing of the voltametric system; preferably, the mounting arm 385 is configured so as to hold the measurement cell 322 (or 302) in a manner (a) that facilitates sensor module selective attachment, removal and replacement, without having to disassemble other system components, and (b) that permits ready external visual inspection of the state of the measurement cell 383 (e.g., with the measurement cell being made of clear non-reactive plastic so as to permit non-invasive inspection of any accumulated surface particulate and state of the metal electrode conductors). To this effect, threaded bores 389A and 389B in the measurement cell block 322 can be used to provide fluid ingress/egress channels (e.g., potentially including a channel for overfill protection), as well as any additional sensors that may be desired (for example, an image sensor of some type to permit remote inspection of measurement cell/electrode condition, or detection of degradation based on automated processing, e.g., as assisted by image processing or other monitoring software). The selection both as to number of such additional sensors/channels for access to the measurement cavity 303 and the number of bores need to mount those sensors is a design implementation decision, and is typically within the level of ordinary skill in the art. In the depicted design, the depicted components are typically contained within the housing for the voltametric system, but are advantageously accessed and rendered visible by removing or opening a panel of that housing. To this end, in the example of FIG. 3D, the mounting arm 385 attaches to a back wall of the housing (or an internal structural member) in the direction of arrow 386, e.g., with screws engaging the mounting arm in the reverse sense of arrow 386 and through the back wall of the housing (not shown); this holds the mounting arm in place relative to the system housing and it positions the various other depicted components for ease of access and individual, modular replacement.

The measurement cell 322 (or 302) is seen at the right side of the FIG., and shows a bore 313A for receiving the auxiliary electrode (not shown), as described earlier, with a similar bore being featured on the bottom of the measurement cell (but not visible in this FIG., i.e., see FIG. 3A or 3B). The measurement cell in turn engages the mounting arm 385 along the direction of arrows 391, with screws (not shown) being inserted through holes 388 into the mounting arm (e.g., in the direction of arrows 359), so as to screw in to the measurement cell 322 (or 302) and hold it snugly in place against the mounting arm 385. Similarly, the opposing side of the measurement cell block features screw holes 393 to permit mounting of a transducer module to the measurement cell, with the transducer emitter surface being inserted into cavity 323 so as to direct ultrasound toward the conductive surface of the working electrode, represented by numeral 305'. As noted earlier, the working electrode module 353 is inserted into the measurement cell 322 (or 302) in the direction of arrows 359 and passes through a central bore 394 in the mounting arm 385 so as to snugly engage the measurement cell. It is not directly fastened to the mounting arm (i.e., a design feature which permits selective electrode module replacement without detaching the measurement cell 322 (or 302) from the mounting arm), but is instead attached by means of the locking nut (not shown in this FIG., but as described above, in connection with FIG. 3C).

Reflecting on the design of the measurement cells depicted by FIGS. 3A-3D, and their integration into a voltametric measurement system, it should be observed that the depicted designs optionally provide for (a) each of access, (b) visual inspection of measurement cell and electrode state without having to disassemble the measurement cell or remove its modules, (c) modular removal of (and cleaning of, buffing of, and/or replacement of) the working electrode and/or the other electrodes without having to necessarily replace or remove other modules, (d) use of electrodes where all conductors are directly immersed in the measurement sample, and (e) a configuration where ultrasound, rinses, and/or chemicals can be applied in-situ for electrode renewability and maintenance. More specifically, the specific design represented in this figure permits directing of ultrasound uniformly over the entire conductive surface 305' of the working electrode, with a broad ultrasound emitter surface efficiently delivering ultrasound energy in close proximity to that surface 305'. As should be appreciated, these various features individually and collectively provide for substantial advances in voltametric system and/or electrode lifetime and serviceability, especially for field-based applications.

Figure 4:
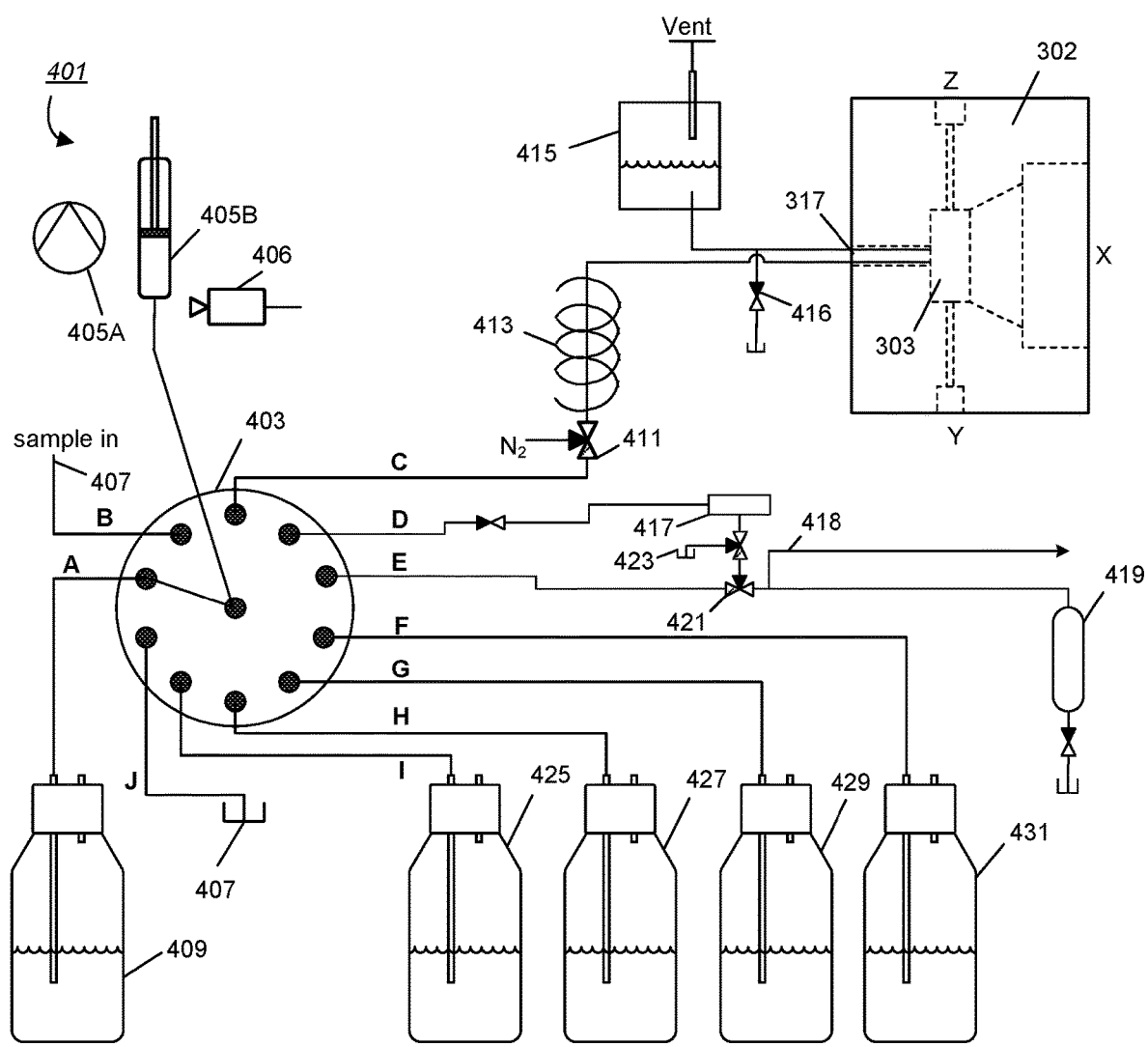
FIG. 4 provides a system schematic diagram showing one non-limiting example of fluidics management in a repeatable-use voltametric measurement system.

FIG. 4 provides a system schematic diagram showing one non-limiting example of fluidics management in a repeatable-use voltametric measurement system. More specifically, FIG. 4 provides an illustrative diagram 401 that shows a prefabricated measurement cell (such as block 302 from FIG. 3A), a fluidic transfer or actuation mechanism (comprising a pump 405A or a motion-controlled syringe 405B, and associated tubing), a rotary selector 403, a degassing unit 413, a filter or switch 417, and containers 409, 425, 427, 429 and 431 for various solutions. In the depicted embodiment, the electronic control system (not seen in the FIG.) controls actuation of the rotary selector (i.e., by digitally commanding source/destination A-J), with the fluid actuation means (e.g., rotary selector 405B) being used to draw fluid back-and-forth through the rotary selector in a controlled, precise manner; to this effect, the depicted fluidic transfer mechanism utilizes a sensor 406 (e.g., optical or otherwise) and associated feedback for precisely detecting fluid level (e.g., within the motion-controlled syringe 405B), thereby enabling very precise fluid draws and injections. To provide but one example, as discussed earlier, one measurement application might mix exactly 4.50 mL of measurement sample with 0.50 mL of buffer solution (e.g., 2.0M hydrochloric acid, or HCL); the depicted fluidic transfer mechanism, e.g., motion-controlled syringe, performs precise fluidic measurement so as to effectuate the required precision. The fluidic transfer mechanism is also commanded to periodically, intermittently or on an ad-hoc basis draw a sample of the liquid of interest (e.g., a sample of well water "every two hours"), also to the required or desired volume, via inlet 407; an automated sample extraction mechanism will be described further below in connection with the discussion of FIG. 7, e.g., such a sample extraction mechanism can draw a relatively large sample (e.g., 45 mL), representing the source being measured at one point in time, and then this relatively large sample can be used to feed successive measurements (e.g., a first 4.50 mL draw to test for presence of excessive organics, a second 4.50 mL draw for arsenic measurement, a third 4.50 mL draw for selenium measurement, and so forth), each representing source liquid constituency at the time the sample was originally drawn. As should be understood, software (instructional logic) is relied upon to control the various depicted amounts, so as to effectuate the required precision-draws/injections, and sequencing.

Note that FIG. 4 contemplates application of the voltametric measurement system to measure diverse metals, e.g., each of arsenic and selenium concentration, in respective measurement cycles. To this effect, the various solutions stored in containers 409, 425, 427, 429 and 431 can represent solutions, buffers or reagents needed for different measurement chemistries. For example, container 425 can be used to store 0.20M HCL (hydrochloric acid) for use in arsenic concentration measurements, while container 427 can be used to store 2.00M HCL for use in selenium concentration measurements. Solutions for many other chemistries can be stored, and the system is not limited to the use of two such solutions, e.g., N different buffers/reagents may be stored, for use in M different measurements of concentration of J different metals, where each of N, M and 1 can be greater than or equal to two. As noted earlier, in one embodiment, one or more reactions can be triggered, for example, to convert metals from one form to another (e.g., Se(VI) to Se(IV) or As(III) or As(V) to As(0)), with these processes being selectively used so as to permit discrimination of individual species/forms (see PCT application No. PCT/US17/38022, published internationally as WO2018013293, and in the US as US Publication No. 20200003745 (U.S. Ser. No. 16/309,009), which is hereby incorporated by reference). Container 409 can be used to store deionized water for use in rinsing the measurement cell 302 (or 322) so as to assist with its renewal for ensuing measurements, while containers 429 and 431 can be respectively used to store one or more standards and/or one or more cleaning solutions. Once again, each standard and/or cleaning solution can be applied on a selective basis for testing electrode health and/or cleaning the measurement cell and the electrode surfaces, depending on the analyte being measured and the metal being tested for. Advantageously, each of the containers 409, 425, 427, 429 and 431 is made to be user-serviceable, with alerts being generated (see FIG. 2, numeral 222) when levels run low. Note that FIG. 4 also depicts a trap or drain 407, to remove spent fluid from the system; in one embodiment, this outlet is connected to a discard container (not shown) which similarly may be removed and discarded by an operator (e.g., pursuant to an alert) when the container is full. In other embodiments, where chemistries safely permit, spent fluid can be coupled directly to a conventional drain. Such a design facilitates automated and/or remote control operation on an intermittent, periodic or ad-hoc basis with only occasional operator access needed to replace chemicals/solutions and/or discard waste, or otherwise for system maintenance.

For processing of samples, signals from the electronic control system (e.g., processor control signals) command change of the rotary selector to port "C" and cause the motion-controlled syringe to push the measurement sample through the degassing system 413, to deoxygenate the solution (e.g., oxygen typically creates substantial measurement noise and is advantageously removed for many applications of interest). The degassing system comprises a coil that creates turbulence, and the injected solution passes through a 3-way valve 411, at which point nitrogen gas (or another suitable gas) is injected to help force oxygen out of the system as it passes through the coil; nitrogen injection is similarly governed by a control signal (not shown) provided to the three-way valve by the electronic control system (also not shown in this FIG.). The measurement sample enters the measurement cell 302 via a port 317, and with any residual gas expunged using the depicted vent 415; in addition or alternatively, a pressure-actuated value 416 can also be used. Both the vent 415 and the valve 416 represent optional means for providing overfill protection. For analyte inside the measurement chamber 303, the electrodes (XYZ) are then controlled as described earlier to carry out voltametric processes and measurements. In FIG. 4, the letter "X" is used to designate the working electrode, the letter "Z" is used to designate the auxiliary electrode and the letter "V" is used to designate the reference electrode. Once again, as depicted in the FIG. and as described earlier in connection with FIGS. 3A and 3B, the measurement cell can optionally (and advantageously) feature a modular design, with electrodes separately serviceable from one another, and electrode conductor surfaces that are directly immersed in the analyte within the measurement cell 302 (or 322), i.e., in a "half-cell-less" (i.e., non-insulated) design.

It was earlier noted that in some applications, the depicted system is restricted to applications where the measurement sample is relatively "clean," i.e., not having undesired organics or other substances that might foul the exposed conductors of electrodes, or otherwise interfere with proper reference electrode function. Note that a "clean" analyte in this context is not restricted to ground water, e.g., it can potentially encompass waste water, manufacturing waste, potable water, and nearly any other type of liquid as long as a sufficient expectation exists as to the chemistry of the sample that it does not include substances that will plate the reference electrode, or otherwise require reference electrode cleaning beyond the capabilities of the system. If these expectations exist, the voltametric system can potentially be directly applied to automated measurement without need for special filtering, testing or switching functions. Note that FIG. 4 illustrates the presence of these optional functions, e.g., if the sample chemistry is unknown, the system can also feature a filter or sensor 417; note that this filter or sensor 417 can also be positioned upstream of port "B" of the rotary selector 403. In this regard, a filter can be used to advantageously remove unwanted substances (e.g., organics), for example, with new samples being driven through element 417, through a three-way valve 421 and into a storage vessel 419. Conversely, element 417 can instead be configured as a sensor, e.g., if unwanted substances are detected by the system to be present, the measurement sample can be discarded through drain 423, or can instead be driven to another system (e.g., a conventional voltametric system with an "insulated" glass/ceramic reference electrode, not shown), via path 418. Note that typically another sensor is used to detect these substances, so as to safeguard the voltametric system from contamination or the need for additional cleaning. Other alternatives also exist. If appropriate, filtered sample (or samples which pass tests) can be drawn back through the rotary selector, via valve 421 and port "E" and then into the measurement cell for testing.

The depicted measurement cell 302 is designed to be a sealed, non-reactive unit that can be partly used for intermingling various injected solutions, e.g., 4.50 mL of measurement sample via rotary selector port "B" or "E" and 0.50 mL HCL (e.g., via port "I," "J" or one of the other ports as appropriate). To mix these fluids, as appropriate, the motion-controlled syringe 405B (or other fluid actuation means) operates in reverse, drawing out any injected solution(s) back through the degassing unit (which helps mix all fluids)

and it then operates forward again to re-inject fluids into the measurement cell. For example, the motion-controlled syringe 405B can be sequentially controlled by the electronic control system to first inject a measurement sample, later followed by the desired volume of buffer, all while nitrogen gas is injected to deoxygenate the respective fluids; the motion-controlled syringe is then actuated to draw the sequentially-injected fluids out together, using back and forth strokes as necessary to pass the fluids through the coil to perform mixing; the syringe then finally pushes the mixture back into the measurement cell for measurement. The same process can be applied when any standards are injected, e.g., to mix in the standard(s) for one or more "spike tests" (e.g., using a standard with known metal constituency, for example, stored in one of the containers 429 or 431).

When it is time to drain the measurement cell following a measurement cycle, this is accomplished by controlling the rotary selector 403 and the motion-controlled syringe 405B to draw solution out of the measurement cell, and optionally then redirect the drawn solution out of port "J" of the rotary selector to a drain 407; note that in many embodiments, the drain is a waste disposal unit where spent fluid is collected and then discarded in an environmentally-friendly manner. Port "A" of the rotary selector can also be used to inject a rinse or other cleaning solution (e.g., a solvent, deionized water, or whatever solution is desired) into the measurement cell via port 317 so as to remove residual analyte (or particulate, e.g., removed via use of ultrasound or application of a cleaning solution), as part of one of the optional cleaning cycles.

As previously mentioned, in one embodiment, there can be more than five consumable solutions, i.e., the measurement system can include an array or carousel of different buffers, reagents or cleaners, to provide for alternate chemistries, each coupled to a different port of the rotary selector. To perform measurement, software directing the electronic control system selects the analyte of interest that is to be measured, chooses the correct solution, buffers and standards, and their associated volumes, and controls the rotary selector 403 and motion-controlled syringe 405B (or pump 405A) so as to inject the proper sequence and combination into the measurement cell. While FIG. 4 depicts five solutions, this depiction should be understood to symbolically represent any desired number or combination of solutions, standards, cleaners, buffers and so forth. For the depicted embodiment, assuming only a single analyte will be measured, the solutions might include: (a) a buffer 425 used to select the chemistry of interest; (b) a standard (e.g., in container 427) used for a spike test or other tests or calibrations; (c) one or more cleaning solutions in containers 429 and 431 to remove particulate or particulates of interest; and (d) deionized water in container 409, for rinsing of the various fluidic components. Each of these, when spent, is collected in the drain 407 (subject to any proper disposal requirements). Typical cleaners, depending on application and measurement chemistry, can include acids, bases, solvents, chelating agents, water, saline, or nearly any other suitable material; as these materials will periodically be replaced by an operator or service personnel (e.g., to install a new supply of cleaning solution), these cleaners can advantageously be chosen so as to be benign, e.g., 0.1 molar nitric acid (instead of a higher concentration that might be dangerous to handle or create noxious fumes).

Reflecting on the system just described, it is expected that such a system can be cycled hundreds to thousands of times (i.e., ideally indefinitely) without need to remove, replace or otherwise manually service the electrodes or measurement cell. In one embodiment, the various components are made modular or self-contained, e.g., such that system components including electrodes may be easily replaced by a customer or otherwise in-situ, and such that various buffers, solutions, cleaners, standards, chemicals and other consumables can be replaced easily by customer personnel. The system is then prepared for completely automated and/or remote-controlled operation.

Figure 5A:
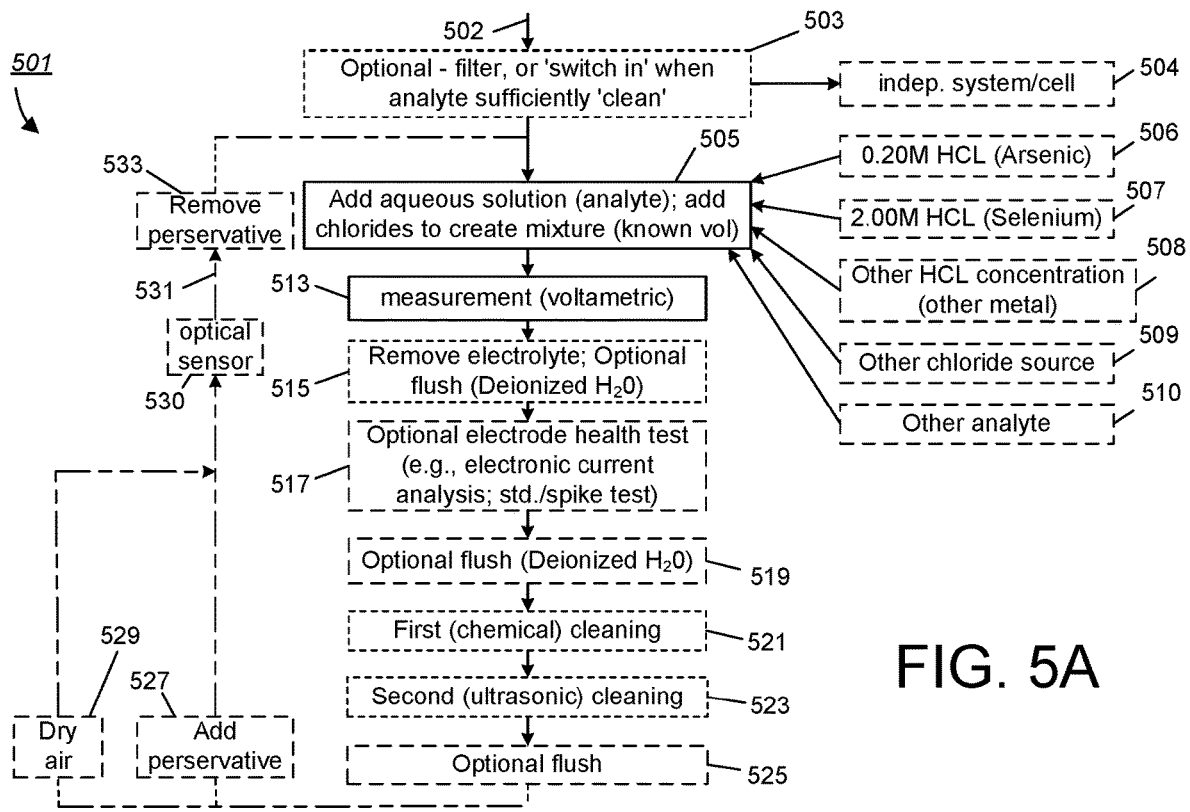
FIG. 5A shows a flow chart for one embodiment of voltametric measurement techniques introduced by this disclosure.

FIG. 5A shows a flow chart for one embodiment 501 of voltametric measurement techniques introduced by this disclosure. The process begins at numeral 502 where it is assumed that a sample of a liquid has been taken. Again, in some applications, this sample represents a water source that is relatively "clean," meaning that the voltametric system and techniques described herein can be applied with an expectation that the liquid will not contain substances that might befoul the electrodes or otherwise significantly impede the measurement chemistry that is at-issue. As referenced elsewhere herein, applications are contemplated besides water. It is also possible to use the voltametric system or techniques described herein in the measurement of substance concentration where these assumptions are not satisfied; for example, as indicated by an optional block 503, a filter can be used to filter substances from an incoming sample which do not satisfy these assumptions (e.g., certain organics), with the resultant filtered liquid then being measured. Alternatively, as also indicated by this optional block 503, a sensor and switch can be used, e.g., to test for the presence of substances that violate input constraints, and responsively then filter the same (or switch sample measurement to an alternative measurement system) if the mentioned constraints are violated. It is also possible to measure samples having substances which do degrade electrodes or interfere with their function, e.g., if provided chemical or ultrasonic cleaning mechanisms are capable of cleaning or renewing the electrodes and/or measurement cell given the substances at-issue. Other possibilities will also occur to those having ordinary skill the art.

As noted earlier, techniques discussed herein provide for a voltametric system and related devices and techniques that are amenable to high-life-cycle usage, particularly in-situ, in automated, field-based applications. To this end, the system advantageously can be configured to "automatically" and intermittently (e.g., periodically or according to another calendared basis) draw samples to test for excessive presence of an analyte. To provide an example, selenium can exist in various forms including as selenium-4 (Se(IV)) and selenium-6 (Se(VI)). A voltametric system described herein can be configured to test for total selenium and/or each of these forms independently using suitable processes for isolating, converting and measuring these various forms (see, e.g., commonly-owned patent application no. PCT/US17/38022, filed on Jun. 16, 2017, for "TECHNIQUES FOR TOXIC METAL DETECTION AND SPECIATION IN WASTE WATER AND IN TREATED WATER," filed in the US under 35 USC § 371 and published as US Publication No. 20200003745, which has already been incorporated by reference). As a non-limiting example, measurement chemistry in one application might measure Se(IV) presence, specifically, and Se(VI) presence can be deduced dependent on the difference between (a) a first measurement of Se(IV) only, and (b) a second measurement, wherein a second sample is first chemically processed to convert Se(VI) to Se(IV), and wherein total Se(IV) is then measured. Other computational methods can be used for isolating other metal forms of interest, e.g., As(0), As(III), As(V) and other metal forms. In connection with the measurement of selenium, for example, a governmental regulatory body such as the US Environment Protection Agency ("EPA") might set a maximum concentration of a substance, typically expressed as parts-per-million ("PPM") or parts-per-billion ("PPB"). Because the constituency of a source (e.g., a water source) might change over time, it might be desired to remeasure the source periodically (e.g., every two hours) or on some other basis for one or more metals or metal compounds or forms. Systems of the type described herein can therefore be advantageously employed in a water distribution network (e.g., potentially at multiple different points in a municipal water company's distribution network) to each monitor for the presence of one or more specific substances. Measured concentrations can be logged and/or reported and/or used to sound operator alarms or take other actions as necessary; for example, if a particular substance is to be present at a concentration of no more than 5.0 PPB and measurement reveals that this threshold is exceeded, the source of the analyte can be treated to reduce concentration of the substance, an operator alarm can be triggered, a source supply can be switched (e.g., a potable water supply can be switched to change dependence from ground water to river water, or vice-versa), and/or other actions can be taken. As indicated by numeral 504, to facilitate in-situ applications such as these, the voltametric system and techniques described herein can be configured as one or more independent systems and/or measurement cells, each adapted for use in such an application.

As referenced by numeral 505, measurement of a specific metal is performed using techniques introduced above. That is, the sample is introduced in the form of an aqueous solution. An electrolyte is then specially added (e.g., to provide for proper operation of the reference electrode), in the form of a buffer solution to create a mixture. As indicated by the FIG., each of these solutions, the sample and the buffer, are added in known, relative quantities, for example, 4.50 mL of sample and 0.50 mL of buffer, to provide a known volume for the mixture (e.g., 5.00 mL); concentration of the analyte of interest is then measured using voltametric techniques. Nearly any analyte is contemplated by this disclosure, particularly metals that are suitable for concentration measurement by voltametric techniques, subject to use of a suitable electrolyte and measurement chemistry. For example, numerals 506-510 refer to some specifically-contemplated applications. In one such application, referenced by numeral 506, the techniques introduced above are applied to the measurement of arsenic (e.g., As(0), total arsenic, or another specific form of arsenic (e.g., As(III) or As(V))). In such a case, one chemical process contemplated by this disclosure adds as the buffer solution 0.50 mL of 0.20M HCL in order to perform voltametric measurement; other acids (or other substances, such as bases) and associated concentrations can be used depending on the chemical process at-issue. Similarly, numeral 507 refers to measurement of one of the forms of selenium (or total selenium) using 0.50 mL of 2.00M HCL, or another suitable buffer or reagent. As indicated by numeral 508, in a process which adds hydrochloric acid (HCL), a different volume and/or concentration can be used, e.g., to measure concentration of other forms of these metals or another metal analyte potentially present in the sample. Per numeral 509, it is also possible to add a buffer other than an HCL solution, to provide a different source of chlorides for use as part of the (reference electrode) chemistry. Per numeral 510, and as noted earlier, nearly any analyte can be measured, subject to the use of suitable chemistry.

Voltametric measurement is then performed, as referenced by numeral 513, using one or more voltages, voltage pulses, voltage slopes, or other forms of measurement. In one embodiment, the voltammetry process can be a stripping voltammetry process, but this is not required for all embodiments; in other embodiments, different types of voltametric devices can be used. Similarly, the techniques introduced by this disclosure do not preclude the use of variations, or different components or different parts than introduced above; in one possible application, the techniques disclosed herein are applied to a dropping mercury electrode-based system (e.g., where the working electrode is expressed as a renewable liquid mercury hemisphere).

When measurement is complete, per numeral 515, liquid is then drained from the measurement cell including electrolyte (e.g., chlorides), so as to remove them from the surface of the exposed conductor of the reference electrode. The measurement cell (and various electrode surfaces) are then advantageously rinsed with deionized water, for example, as part of a sequenced, automated process as introduced above in connection with FIG. 4, with the reference electrode then being left exposed to dry air or with the measurement cell being filled with another preservative until ensuing measurement. In one application, CDA can be used as a preservative, while in another, deionized water or a saline solution can be used. As indicated by numeral 517, an electrode health test may also be performed, to test an assumption that the three electrodes are operating correctly. For example, as indicated by the FIG., in one embodiment, a "spike test" is performed, where (following sample measurement), a standard having a known concentration of the analyte is then added to the existing sample, and a new measurement is made; measurement results which deviate from predicted values may be symptomatic of malfunctioning electrodes, or electrodes which require cleaning and, in one embodiment, the results can be optionally analyzed and can trigger automated diagnosis and/or action, and/or the automated sending of an email, text or other message to a human operator. In another embodiment, instead of employing a spike test, a standard is once again added to the cell and measured (i.e., by itself), with system health being measured depending on results; the standard can be optionally diluted (e.g., using deionized water) and then remeasured, to base diagnosis on measurement, of multiple, different analyte concentrations. For measurements which require mixing, the apparatus illustrated in FIG. 4 can draw sample and standard back and forth through mixing coil 413, and otherwise into a container (e.g., 419) as necessary to achieve proper mixing prior to measurement. Many other examples of chemistries, processes and potential analytes will occur to those of ordinary skill in the art. Following any such testing (whether using the original sample solution or otherwise), the measurement cell can again be flushed, per numeral 519.

Numerals 521 and 523 refer to optional cleaning processes. That is, it was mentioned above that one advantage presented by the techniques introduced herein is to enable cleaning processes that can be further used to enhance electrode/cell/system useful life and/or serviceability. Per numeral 521, chemicals can be introduced into the measurement cell as necessary to clean or otherwise renew electrode surfaces (i.e., including without limitation the surface of the reference electrode conductor). In one embodiment, chemicals are used which remove oxides from conductor surfaces, or which would be otherwise incompatible with the use of glass or ceramic surfaces present in a conventional "insulated" reference electrode design. In another embodiment, it is possible to use ultrasonic cleaning as a separate cleaning process 523, either in lieu of or in addition to any chemical cleaning process. Ultrasonic techniques, in particular, can be enhanced with a measurement cell design that proximally positions a working electrode surface and an ultrasound emitter surface, in parallel to each other at a distance of less than one-half-centimeter, with the ultrasound emitter surface overlapping the entire working electrode surface, so as to deliver uniform ultrasound energy to the entire useful surface of the working electrode; such a design was shown in FIG. 3B. The serviceability of the system/cell/electrodes can also be enhanced using the modular design of FIGS. 3A and 3B, by permitting individual electrodes, particularly the working electrode, to be independently removed and replaced or serviced (for example, via a polishing or buffing process). Following any cleaning process, the measurement cell and electrode surfaces can once again be automatically rinsed, as indicated by numeral 525.

Note that FIG. 5A also shows some further optional techniques. First, per numeral 527, as was referenced above, a preservative can optionally be added to the measurement cell and any exposed electrode surfaces, to the extent desired. In one embodiment, per numeral 529, the measurement cell and/or electrode conductor surfaces are left exposed to dry air. Note that with a design that leaves a "half-cell-less" reference electrode surface exposed to dry air, dry out of the reference electrode is not a problem, i.e., a "half-cell-less" design which adds chlorides for each measurement and does not rely on a dedicated source of chlorides as part of the electrode structure, and is therefore not subject to the dry out problem which typically plagues insulated electrode designs. Per numeral 530, an optical sensor can be used for the automated or manual remote inspection of electrode health. For example, an optical sensor screwed into the measurement cell (as was referenced above in connection with FIGS. 3A and 3B) can send images of the measurement cell to a remote human operator for visual inspection of electrode (and measurement cell) state. Alternatively or in addition, image processing software (or light processing software) can be used to detect accumulated particulate and/or presence of unwanted metal oxides. Other alternatives are also possible. As referenced by numeral 531, the system and cell and electrodes are via these processes renewed for use in ensuing measurement cycles, all potentially without any operator involvement. Per numeral 533, if any preservative was used in the measurement cell, it is once again removed (and the cell rinsed) prior to an ensuing measurement cycle.

Reflecting on the principles discussed above, the techniques presented in FIG. 5A enable voltametric measurement chemistries which can be predicated on the addition of chlorides for use by the reference electrode with each measurement cycle, followed by draining of both the measurement sample and these chlorides, with a reference electrode thereafter being renewed for an ensuing measurement cycle (e.g., via a rinse with deionized water, and leaving the reference electrode exposed to dry air in between measurements). In one embodiment, these techniques feature optional processing (e.g., filtering) and the addition of an HCL buffer to a measurement sample, to enable/facilitate proper reference electrode operation and the formation of silver-chloride on the reference electrode surface during measurement. In one application, for example, these techniques can be used to measure selenium concentration, for example, by adding processing sample to reduce, remove or convert substances, e.g., a reducer as necessary or desired to the measurement sample to convert Se(VI) to Se(IV), or conversely, by removing Se(VI) from the measurement sample. One then measures Se(IV) presence in the processed sample. In this regard, it was found that HCL concentration of between 1.00 and 6.00M provides an effective reducer with residual chlorides providing a suitable precursor for proper reference electrode operation. Similarly, arsenic can be measured, e.g., by treating the measurement sample with sodium thiosulfate solution to reduce electrochemically inactive As(V) (arsenate) into As(III), with the reaction being speeded by the presence of acidic media, and with 0.20 M HCL foster a high reduction rate while minimizing self-decomposition of thiosulfate. The As(III) can then be measured with voltammetry, with residual chlorides ones again providing a precursor for proper reference electrode operation. Each of these reactions contributes chloride ions to the measurement process, which then combine with the silver or silver chloride wire of the reference electrode conductor to form silver-chloride (AgCl) during the measurement process, providing for a stable reference electrode environment. In other words, advantageously, techniques discussed herein are used to contribute chlorides with each measurement process which then form AgCl and provide for a stable reference electrode environment. As noted earlier, the chlorides are removed with each measurement, such that the reference electrode conductor can be left in a stable state (e.g., a dry or preserved state) in between measurements. Advantageously, a single voltametric design (and supply of a suitable range of reducers, buffers, reagents and so forth), enables a single system to measure concentrations of multiple, different metals and/or metal species, e.g., every two hours or on another intermittent basis.

Figure 5B:
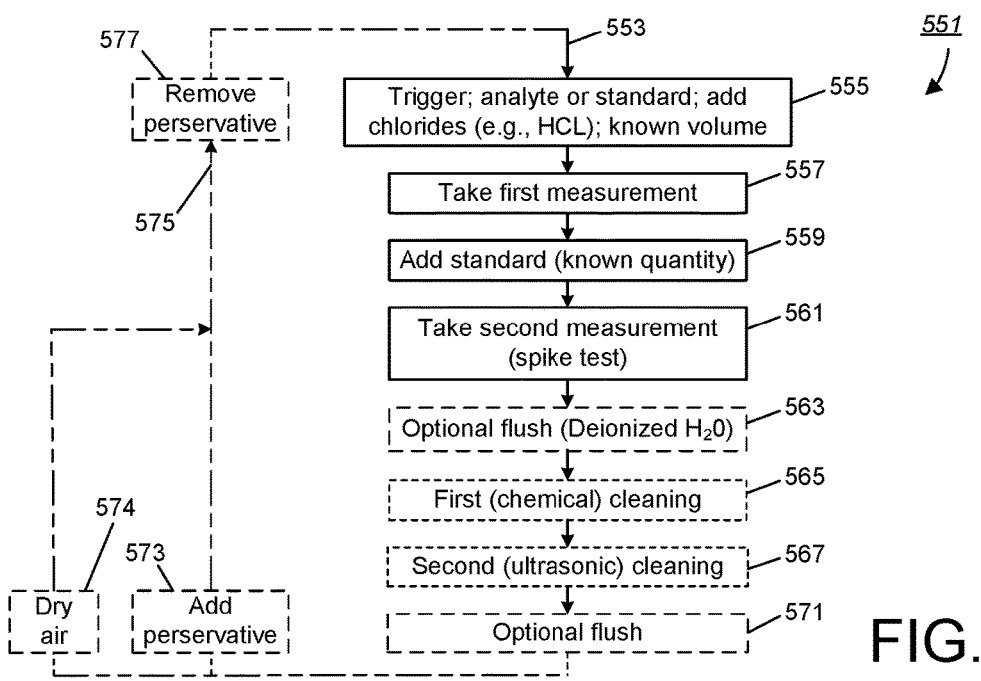
FIG. 5B shows a flow chart for one embodiment of system calibration techniques that can be used in a repeatable-use voltametric measurement system.

FIG. 5B shows a flow chart for one embodiment of system calibration techniques that can be used in a repeatable-use voltametric measurement system. This embodiment is generally designated by numeral 551.

More specifically, the method starts at 553, where an aqueous sample of specific volume is received for measurement. Note that an aqueous solution can be prepared or obtained in many different ways, for example, either natively received as a substance that is directly to be measured (e.g., potable water or waste water, blood, or indeed, any other type of liquid) or otherwise received in a first form (e.g., air) with a specific substance (e.g., a contaminant) eluted to or transferred to an aqueous solution as part of a sample preparation step. Whichever preparation methodology is used, as indicated by numeral 555, a buffer containing chlorides (and optionally a reagent or reducer of some type) is then added to the aqueous solution to select the specific chemistry that will be the subject of measurement and to produce a mixture. Note that in some embodiments, a mixing step can also be employed to ensure measurement of a homogeneous mixture, and in other embodiments, the mixture can be heated, chilled, or otherwise processed or allowed to react to any desired degree prior to measurement, as suitable to the selected chemistry. In a typical application such as a water metrology application, the buffer and/or any reagent can be added to emphasize a particular material (e.g., a specific metal) that is to be measured, to facilitate ionic or other charge transport involving the desired analyte under the influence of a potential difference. This measurement is effected by a first voltametric measurement (557) taken of an electrochemical property of the aqueous solution/mixture (i.e., generally current flow).

In a laboratory setting, a measurement system might be the subject of frequent system calibration (i.e., of electrode sensitivity), such that when a substance of interest is later measured, the measured electrochemical property can immediately be processed using stored calibration results to directly yield analyte concentration. In the depicted embodiment, such an advance process is not used; rather, in order to facilitate repeated, automated measurements of a particular substance of interest (e.g., copper concentration in a drinking water supply), a "spike test" is performed (561) following each measurement, where the first measurement just referred to (i.e., of the analyte of interest) is then supplemented with one or more additional measurements following the addition (559) of a known standard of specific volume to the mixture. As the addition of the standard will change measurement results, and as the relationship between analyte presence in the standard and the measured electrochemical property for the standard is known, the concentration of analyte in the aqueous solution can be determined dependent on the results of the additional measurements for the electrochemical property and the relative volume of the aqueous solution and of each added standard. In one embodiment, only one such spike test is performed, while in another embodiment, multiple spike tests are performed and used to assess linearity of the results (i.e., for diagnostic or other purposes). Once the desired number of measurements is performed, cleaning is then performed, by first (563) flushing the measurement cell and then subjecting it to one or more cleaning cycles 565/567. As indicated earlier, these cleaning cycles can include one or more cycles each of chemical cleaning and/or ultrasonic cleaning. Optionally, as indicated by numerals 571, the system can be flushed or rinsed before or after such cleaning. Once again, depending on embodiment, a preservative can optionally be added (573) to preserve electrode state in between measurement cycles, with the preservative then being removed (577) prior to the next measurement cycle; in one embodiment, the electrodes can be left exposed and dry (574) within the measurement cell. Whichever technique is used, the measurement cell and electrode conductor surfaces are preferably rinsed or otherwise renewed (e.g., using occasional cleaning processes) to ensure the reusability of the measurement cell and system in an ensuing measurement cycle, preferably in a manner that can be performed on demand, with little to no delay. The system is then once again ready for an ensuing measurement cycle, as designated by input arrow 553.

Once again, in some embodiments, various forms of sensors or measurements (e.g., voltametric measurements) can be used to verify proper system operation and to take remedial measures to improve performance. For example, a linearity test (and/or other tests, such as an electrical continuity test), can be performed and tested for satisfaction of a threshold amount of error, which can then trigger optional cleaning as just discussed. Alternatively, an image sensor (e.g., a camera or other sensor) can be used to measure mercury properties (e.g., purity, volume and so forth) and alert an operator if a problem exists.

As should be apparent, FIGS. 5A-5B present methods employed by an automated, voltametric measurement system. The represented processes can be automated in the sense that, whether by command or otherwise, a series of sequential steps are performed "automatically," under the governance of an electronic control system, optionally including sample acquisition; the steps are performed in a sequence without requiring manual intervention and can include electrode rinsing, cleaning and/or other renewal. Optionally, such an automatic cycle can be performed on demand (e.g., any time a command from a human operator), in response to detection of another ad-hoc "trigger" (such as detection of a particular, monitored condition) or on an automated, calendared basis (for example, "every hour"). Other alternatives are also possible.

Figure 6:
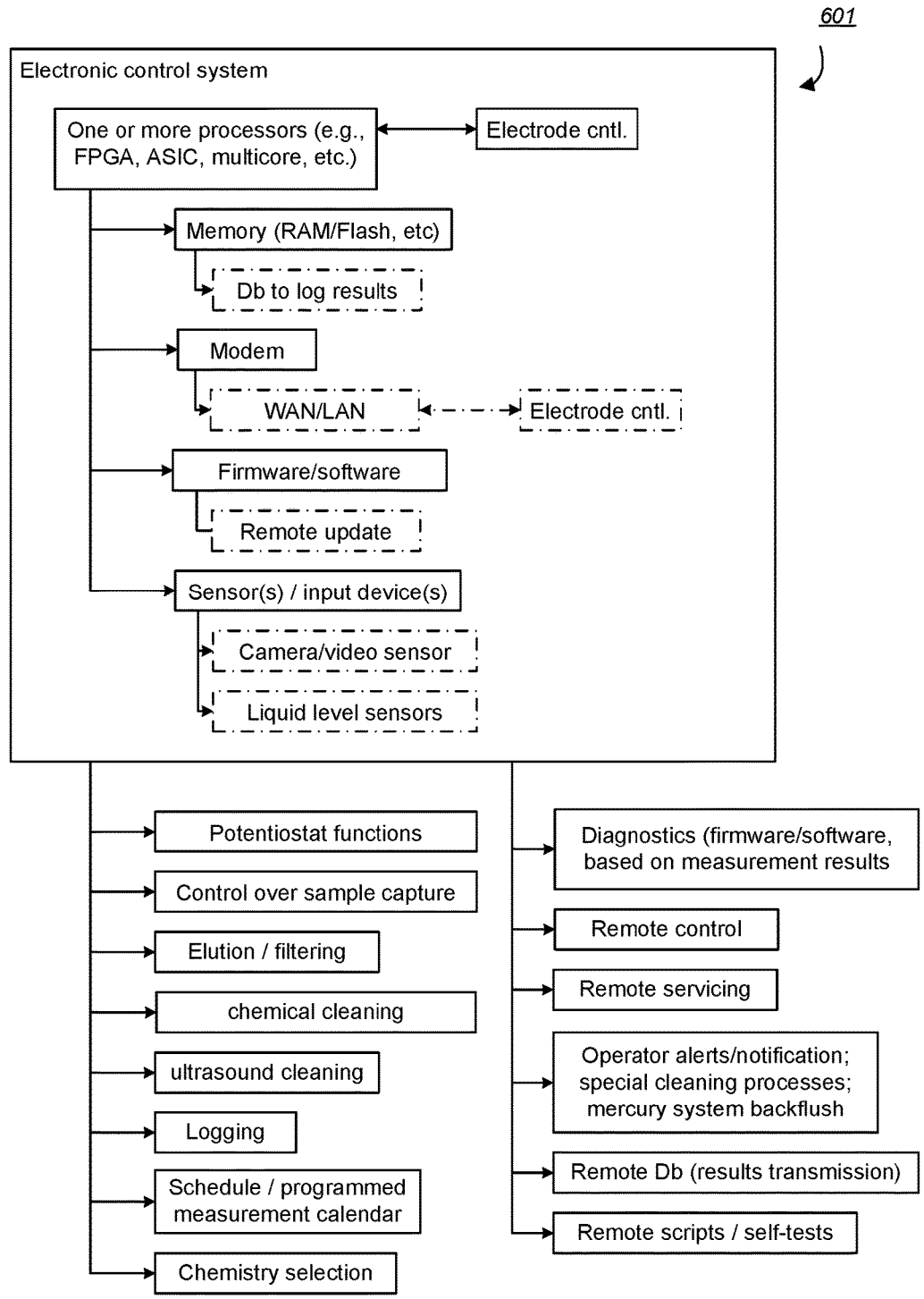
FIG. 6 shows one embodiment of an electronic control system that can be used for a repeatable-use voltametric measurement system.

FIG. 6 shows one embodiment 601 of an electronic control system, used by one embodiment of a measurement system to help automate certain tasks. These tasks are also generally listed at the bottom of FIG. 6. More particularly, the electronic control system includes one or more processors, for example, configured as one or more field programmable gate arrays ("FPGAs"), application specific integrated circuits ("ASICs"), multicore processors or standalone devices running suitable software, scripting and/or firmware, as appropriate. As noted earlier, this instructional logic configures general purpose machines so as to necessarily have functions and operate as application-specific circuits; in the case of the disclosed embodiments, this includes the automated generation of control signals, for example, to provide an automated sequence of processing tasks which include sample measurement and cleaning of materials used for voltammetry (including cleaning and/or electrode renewal as appropriate) to the system. The instructional logic can be stored in on-board or remote memory; this memory also provides space for storage of operating parameters, measurement data and logged results. To provide a non-limiting example, the instructional logic can be coded as referenced earlier so as to cause the one or more processors to implement potentiostat functions and to store voltametric results measured as a result of the selected chemistry. In fact, depending on embodiment, the electronic control system and its associated instructional logic can do much more than that, providing for a myriad of optional functions such as automated control over sample capture and transfer, elution from a filter or concentration medium, reduction and/or other sample processing, cleaning, automated computation of analyte concentration and local or remote logging of results, chemistry selection and implementation of any desired measurement schedule, all as seen at the lower left-hand side of FIG. 6. Similarly, the electronic control system can provide for diagnostic functions (e.g., dependent on once a day self-tests or optional calibrations) and can provide for remote control functions, remote servicing, desired operator alerts and notifications, remedial functions such as special cleaning processes and mercury backflushing, interaction with a remote database, and execution of a myriad of scripts or commands that can be downloaded to the electronic control system. The hardware for performing these functions, in addition to the processor(s), can include local memory (such as random access memory or "RAM," flash memory, a modem for connecting to a wired or wireless wide area network ("WAN") or local area network ("LAN") and sensors used to provide feedback to software that can be used to assess health, interpret results and take corrective actions. These sensors can include, without limitation, an image sensor (e.g., in the measurement cell), and various liquid level or other sensors. In one embodiment, software on-board the electronic control system automatically screens data to detect problems (e.g., such as via the linearity or conductivity tests described earlier); in another embodiment data can be transmitted to a remote service center, e.g., together with an image if supported by the embodiment, with the remote service center interpreting results. In one embodiment, the electronic control system can receive commands or scripts from such a remote service center to take selected ad-hoc measures, such as triggering additional cleaning or specific additional system or sample tests. Such command or scripts can be received via the wired or wireless connection by the depicted modem, and fed to the instructional logic for processing. In one embodiment, as mentioned, the system includes one or more local input devices to visually display results to a human operator or to receive locally-inputted commands. In another embodiment, the electronic control system can be paired with another device, for example, a smart phone or other wireless device, with a downloaded, electively-launched application used for remote control and data monitoring. Many examples are possible and will readily occur to those having skill in the art.

Figure 7:
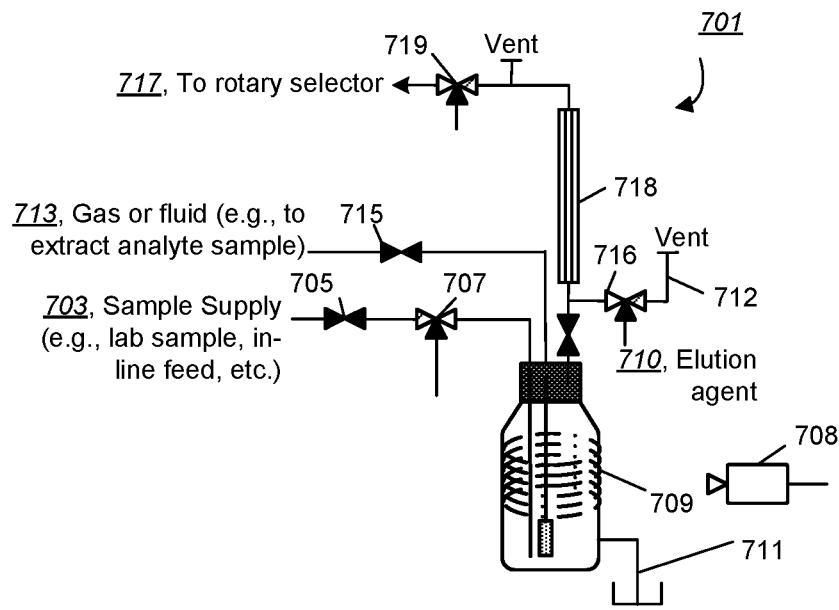
FIG. 7 is an illustrative diagram relating to one embodiment of an automated sample capture or extraction mechanism.
Figure 8:
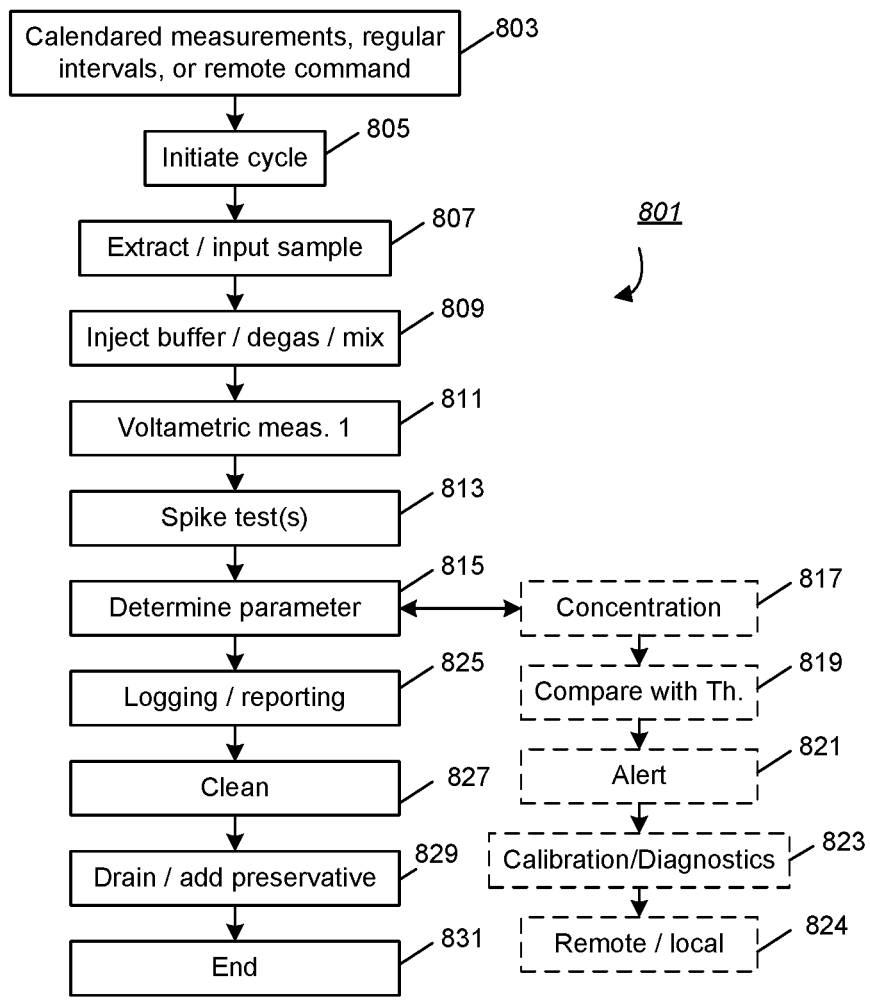
FIG. 8 is a block diagram relating to automated (e.g., calendared or ad-hoc) measurement by a repeatable-use voltametric measurement system.

FIGS. 7 and 8 are used to discuss sample capture and/or cleaning. As alluded to earlier, in one embodiment, a measurement system that uses voltametric techniques can be implemented as a piece of bench equipment, for example, supporting manual sample insertion, with or without ensuing process automation. In another embodiment, a measurement system can be designed for in-line or other automatic forms of sample capture.

FIG. 7 illustrates a sample capture mechanism 701 suited for automated in-line measurement of a fluid, such as a water source, or when it is desired to sample a substance but then elute that substance into another form. Note that even when such an application is limited to water, there exist many different testing methodologies and models, including installation at a municipal water supply for intermittent testing of the levels of metals or other organic or inorganic materials present in drinking water, testing of waste water or runoff water (e.g., mining runoff), testing of sea, lake or river water for pollutants, and so forth; these examples are illustrative and are not limiting. In one installation, a sample vessel 709 is connected to a sample source (e.g., a potable water supply 703) via a set of valves 705 and 707. These valves are electronically actuated (e.g., by an electronic control system) to perform automated sample capture. In another example, extraction can be accomplished using a motion-controlled syringe or pump to draw sample (e.g., instead of relying on pressure of a source of the measurement sample)—for example, a port of the system's rotary selector (as discussed earlier) can be directly coupled, via a valve, to a source. A sensor 708, can be optionally used to provide feedback on the sample volume so as to enable precise sample control. The sample vessel also optionally includes a fluid (gas or liquid) supply input 713. The input 713 permits the sampled substance to be diluted or otherwise mixed with another substance prior to measurement (e.g., for a reaction used prior to measurement, or to otherwise preprocess an analyte for easy detection). The sample vessel also includes an output 717, for example, connected to rotary selector (not shown in FIG. 7) for selective extraction of fluid in the sample vessel. The rotary selector can be selectively actuated to draw a desired amount of solution from the sample vessel 709, with sensor feedback as described earlier. Once the sample is finished, in order to prepare the system for another sample, the sample vessel 709 can be connected to a drain 711 and flushed with cleaner or deionized water (e.g., via injection from the rotary selector and motion-controlled syringe using the input 711 and/or the output 717).

As but one example of eluting analyte from a non-aqueous carrier, the techniques described herein can potentially be used for atmospheric measurement. As with the previous example, a sample vessel 709 is connected with a sample supply 703 (e.g., "air" drawn from a particular location). Once again, a set of valves 705 and 707 are together or independently actuated by the electronic control system to perform sample capture, for example, at a particular time in connection with a calendared measurement event. In this case, however, a gas or fluid is introduced by selective electronic actuation provided by the electronic control system, via supply line 713 and electrically-actuated valve 715. This substance is used to transport the analyte of interest from the sample vessel 709 into an analyte trap or column 718. For example, for many analytes of interest, a gas can be introduced to the captured sample and used to transport by volatile means the analyte of interest into the trap or column 718, where the analyte is adsorbed. Once a particular amount of time has passed, this process is stopped and a 3-way valve 716 is used to introduce an elution agent 710 into the trap or column to then transport the analyte of interest out of the trap or column and to the rotary selector via path 719 and 3-way valve 719. The sample vessel can subsequently be emptied and rinsed, using a combination of venting via 3-way valve 716 and draining via drain 711. Note that a number of different mechanisms can be used alone or in combination to (a) first separate an analyte of interest from the original sample and transfer it to column 718, and (b) subsequently elute or transfer the analyte of interest from the depicted optional column 718 to the form of an aqueous solution suitable for voltametric measurement. In the depicted system, it is contemplated that the aqueous solution can be formed by passing solution through the column as the extraction agent, but gaseous, thermal, chemical or other means can be used for each of these processes; in addition, it is possible to elute the analyte of interest to another capture vessel (e.g., providing output 717 as an input to the elements seen in FIG. 4) and to then form the aqueous solution that will be used for processing and/or measurement.

Many alternatives will readily occur to those skilled in the art. In the case of the depicted elements, these elements can be in one embodiment controlled on a fully automated basis by an electronic control system, for example, to automatically draw samples on a calendared basis, without human involvement. This is not required for other embodiments.

FIG. 8 is used to revisit how these various mechanisms can be used for sample capture, via a flowchart 801. The method begins at 803 where an event is generated corresponding to either an ad-hoc command or trigger to perform a measurement (e.g., entered by a human operator or received via a network connection), or generated in-situ. For example, such a trigger can be generated by an electronic control system that detects passage of a predetermined amount of time, occurrence of a particular date and/or time, or occurrence of another threshold condition. The occurrence of such event causes the initiation of a measurement cycle (805) where a sample is first drawn (807), optionally using feedback to ensure adequate sample is drawn at the appointed time. The sample is prepared, eluted, reacted and transferred as necessary (e.g., using the mechanisms discussed above in connection with FIG. 8) in the form of an aqueous solution suitable for voltametric measurement, and is degassed and mixed with suitable buffer and/or reduction chemistry (809). A first voltametric measurement is then performed (811), followed by the addition of a known standard, via one or more spike tests (813); as discussed earlier, the standards provide a known quantity, and can then be added post-analyte introduction (i.e., via the aqueous solution) to permit derivation of a desired parameter 815. The desired parameter is optionally analyte concentration in the aqueous solution (817); the electronic control system (if it computes this parameter, as opposed to storing or transmitting raw measurement data such as measured current or voltage), can optionally compare the derived parameter with a threshold (819) and generate an alert (821) or perform diagnostics (823) as necessary. A few examples will be illustrative in this regard; for example, if a limit for lead presence in water is determined to be a particular level "K" measured in parts-per-billion, software running on the electronic control system can derive from in-situ measurement the amount of lead currently present in the water, and can sound an operator alarm (e.g., audible alarm, email alert, prerecorded alert, or provide some sort of visual indicator to a desired local or remote destination) or take some other form of remedial action if excessive lead is present. The remedial measure in one embodiment can include closing a valve, running a diagnostic test, taking a fresh sample and/or reperforming measurement, or indeed, any other desired action. As represented by numeral 823, computed results can also be compared to predetermined metrics and used for calibration or diagnostics, i.e., to measure standards, to perform linearity tests, or for other purposes. As represented by numeral 824, any of these things can be locally or remotely controlled, stored, reported or governed.

Per numeral 825, the system then optionally logs all data it acquires, for compliance, regulatory or other purposes. As just referenced, this logging can be local or remote. For example, storage of periodic measurement results can provide trends analysis or other useful information. It can also be important for regulatory or other purposes to retain data to provide accountability or forensics, or because such is otherwise required by law.

Once all tests are completed, e.g., as to numbers of tests, analytes of interest and so forth, the measurement cell is optionally cleaned and/or renewed (827) as described earlier, and the captured sample is discarded. Affected system components (e.g., sample capture vessel, pertinent tubing and measurement cell) are then rinsed as appropriate. In one optional embodiment, residual rinse fluid beneficially keeps the inside of the pertinent tubing, the measurement cell and the pertinent electrodes moist, and preservative can optionally be added to fill these components if a very long period will be used between measurements (i.e., to maintain the health of these elements), per numeral 829. The method then ends, i.e., the system is then prepared to a state where it awaits the next measurement event. As noted earlier, in one embodiment, this entire measurement cycle can be fully automated, without requiring human intervention. In one embodiment, this method can be implemented as a lab process, invoked on an ad-hoc basis by a human operator once a sample has been obtained (e.g., a blood sample used for lab analysis). The human operator initiates the cycle, which is then automatically processed by the electronic control system through to completion. In another embodiment, a continuous loop is performed without the involvement of a human operator (e.g., sample extraction, rinsing and measurement events are entirely automated according to previously-supplied programming). Clearly, other alternatives will occur to those skilled in the art.

As can be seen from this discussion, embodiments presented herein provide a novel, automated way to calculate concentrations of, and otherwise monitor for presence of, individual metals, compounds, species, forms, and so forth, which are of interest. These mechanisms also provide for cooperation among multiple entities, each of which can optionally practice a "piece" of the techniques described earlier (i.e., such that one entity uses software that permits it to interact with software or systems optionally used by another entity). This includes various control processes which can be aggregated at a central location or distributed, depending upon embodiment. As alluded to earlier, a control system may, as part of an in-situ device, part of a local area network ("LAN") or over a wide area network ("WAN,"

e.g., the internet), automatically monitor a substance of interest and take remedial action, for example, by sounding or otherwise triggering an alarm, or by using an electronic control system and the feedback provided by periodic measurements. In one contemplated embodiment, these techniques can be applied to a potable or non-potable water supply; for example, with such an automated measurement mechanism, it becomes possible to immediately adjust chemical treatment upstream in a water sanitation or other process dependent on automated, downstream monitoring. Such a system may be run continuously, 24 hours per day, unattended, with a warning indication or other action if contaminants exceed a specified limit, responsive to a detected maintenance condition, or on another ad-hoc basis.

Figure 9:
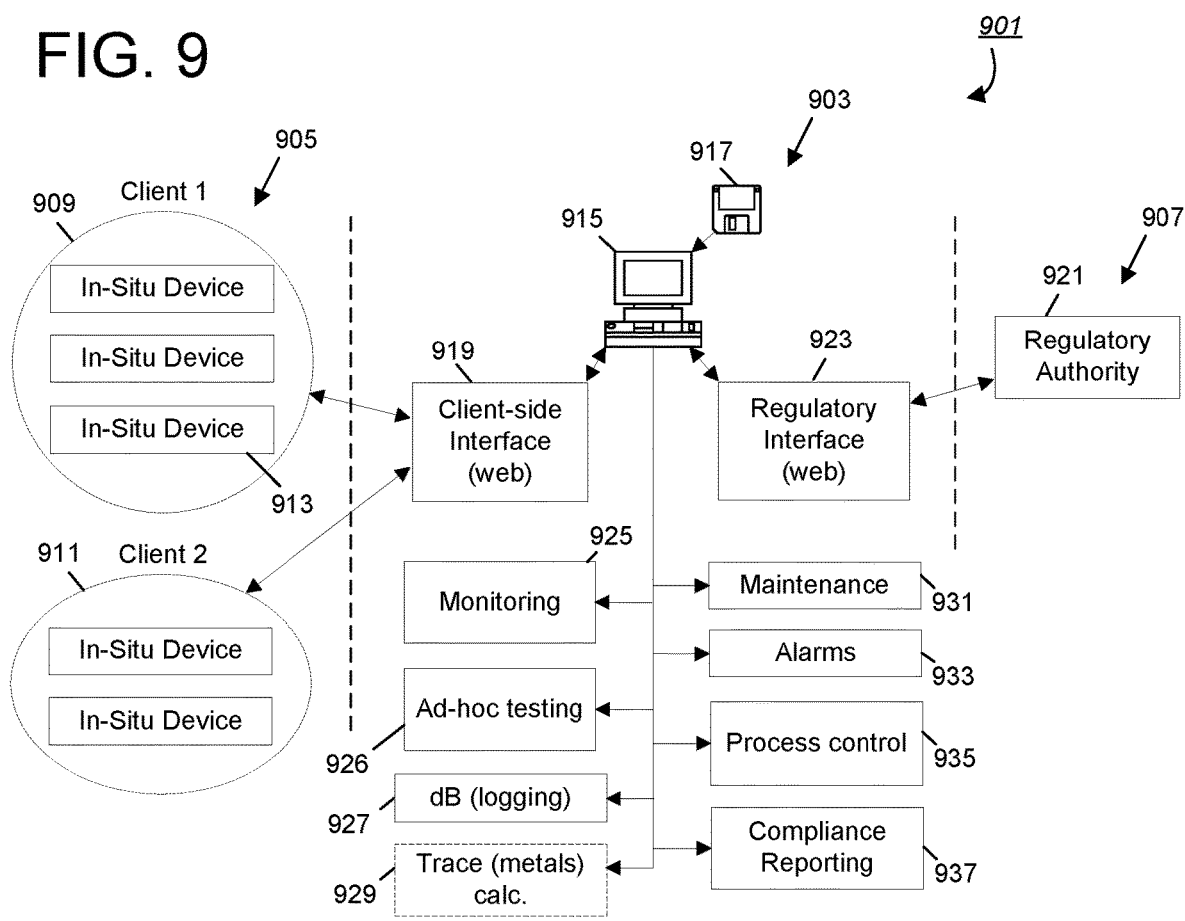
FIG. 9 is a block diagram relating to network-based management of a repeatable-use voltametric measurement system.

FIG. 9 provides a system/networking diagram 901 used to explain a method of remotely monitoring one or more in-situ mechanisms or devices. Once again, measurement of a water supply is used as an application example, but the disclosed techniques can be applied to measurement of any other substance, whether or not fully automated, and whether or not such involves water metrology. More particularly, FIG. 9 is seen to be divided into middle, left and right portions (903, 905 and 907) that respectively represent (a) an on-line or other business that for a fee may automatically monitor a substance (e.g., one or more water supplies), (b) one or more clients of the business (e.g., one or more municipal water companies), and (c) a regulatory authority or other entity that is to monitor results or receive reporting of compliance. FIG. 9 illustrates two hypothetical clients 909 and 911, each of which may be taken for this example to be a water company, and each of which may have one or more in-situ devices 913 for monitoring a particular portion of a water delivery network (only one in-situ device is numerically labeled to simplify the illustration). In this regard, it should be assumed that the method (e.g., the business) is to automatically and/or remotely collect measurement data for the purposes for compliance reporting or other purposes; to this effect, the business 903 includes a supervisory control mechanism 915, depicted as one or more computers running software 917 (e.g., a server system), with this system interfacing both with each client (via a client-side web interface 919), and with a regulatory authority 921 (via a regulatory side interface 923). In one embodiment, the regulatory side web interface may provide a portal for regulatory authorities to remotely audit current and past individual operations (e.g., water supply operations), with further ad-hoc tests being initiated as required, and with the business interacting with regulatory authorities on behalf of each client, if desired or appropriate, in a manner transparent to each client. Each interface 919/923 may permit different access levels and present different authentication requirements (e.g., a specific type or level of PKI authentication). For example, because the client side interface may be used for automated communication with each in-situ device 913, each such device may be made to have an embedded cryptographic key for purposes of authentication; on the other hand, because regulatory interaction may involve aggregated, relatively sensitive data, or for other security reasons, two-factor or other authentication requirements may be used as a predicate for individual access by a remote human user. Regardless of the interface formats, the supervisory system can be configured to perform a number of functions, depicted at the middle of FIG. 9, thereby relieving the clients 909 and 911 from the need to perform these functions themselves, and minimizing the need for on-site presence or inspection by regulatory authorities. As indicated by reference numeral 925, the method may include periodically receiving test data from each one of the plural in-situ devices 913 via the client-side interface 919; each instance of test data may represent an automated process that is initiated by the specific device 913, and/or the supervisory system 915 may also selectively initiate tests. For example, if it is determined that a specific metal ion as determined from a test is out of normal bounds, an ad-hoc test may be commanded by the supervisory control system, as indicated by reference numeral 926. The supervisory control system may perform data base management (927), indexing each set of test data by particular provider, time and date, last known calibration, and any other desired data. As indicated by blocks 931, 933, 935 and 937, the supervisory control system (or a different electronic control system) may also test for and/or respond to maintenance events, generate alarms or take process control actions responsive to comparison of trace levels of various toxic metals or other specific substances against thresholds, and generate automatic compliance reports either for the regulatory authority 921 or a particular client 909 or 911. As further depicted by a dashed-line, optional block 929, if desired, raw data may be reported to the supervisory control system 915, with total and/or individual metal species calculations being performed by the supervisory control system 915, on a remote basis.

As should be apparent from this description, the methods and devices provided above, by facilitating real-time, relatively same, automated analyte measurement, provide for new advances not only in the measurement process, but also in terms of compliance and accountability, potentially changing the way in which water companies, manufacturers, regulatory authorities and/or other entities conduct business. More generally, the disclosed techniques provide for voltametric measurement systems that can be used for a wide variety of applications.

Various alternatives to the foregoing techniques will readily occur to those having skill in the art. To pick just a few examples, techniques mentioned above may be applied using other types of applications, chemistries, analytes or processes; instead of a "current-sensing" voltametric system, for example, techniques discussed herein can also be applied to a voltage-sensing design. Similarly, it is possible to extend the techniques discussed herein to the measurement of concentration of metals other than selenium or arsenic, by way of non-limiting example, to toxic metals, such as selenium, cadmium, lead, copper, arsenic, chromium, beryllium, aluminum, nickel, uranium, selenium, zinc, and to other metals and non-metallic substances. Further, while the discussion above has used the example of stripping voltammetry, it is possible to apply these techniques to many other forms of voltametric and/or other measurement. While various conductor types and surfaces have been discussed above, for example, based on silver, platinum, mercury and/or other substances, it is no doubt possible to change some of or all of these substances while preserving techniques introduced hereby. Many other variations also exist and will occur to those of ordinary skill in the art.

Accordingly, the foregoing discussion is intended to be illustrative only; other designs, uses, alternatives, modifications and improvements will also occur to those having skill in the art which are nonetheless within the spirit and scope of the present disclosure, which is limited and defined only by the following claims and equivalents thereto.

I claim:

1. A measurement method using a voltametric measurement device, the voltametric measurement device having a measurement chamber, a working electrode, an auxiliary electrode and a reference electrode, wherein the reference electrode comprises a conductor surface having at least one of silver or silver chloride, the measurement method comprising, for each of respective measurement cycles:
   using a fluidic transfer mechanism to supply an analyte to the measurement chamber;
   immersing each of the working electrode, the auxiliary electrode and the reference electrode within the measurement chamber into the analyte, such that the conductor surface is placed in direct contact with the analyte;
   adding a source of chlorides to the analyte, to create a mixture;
   performing voltametric measurement of the mixture to detect presence of a metal substance in the mixture; and
   following performance of voltametric measurement, removing the mixture, including the chlorides, from the presence of the conductor surface;
   wherein the measurement method further comprises cleaning the conductor surface in between ones of the respective measurement cycles, using at least one of a fluoride-based substance or an add.

2. The measurement method of claim 1, wherein the method further comprises exposing the conductor surface to clean dry air in between ones of the respective measurement cycles.

3. The measurement method of claim 1, wherein the method further comprises immersing the conductor into a non-saline preservative in between ones of the respective measurement cycles.

4. The measurement method of claim 1, wherein the reference electrode comprises at least one of a silver wire or a silver chloride wire, and wherein measuring the analyte comprises immersing the at least one of the silver wire or the silver chloride wire directly into the analyte.

5. The measurement method of claim 1, wherein the measurement method further comprises cleaning at least one of the electrodes in between ones of the respective measurement cycles, by directing ultrasound energy toward the surface of the at least one of the electrodes, the directing being performed in the presence of the conductor surface.

6. The measurement method of claim 1, embodied as a method of measuring an aqueous sample, wherein each analyte is in the form of an aqueous sample, and wherein said method comprises automatically initiating the respective measurement cycles on a calendared basis and automatically controlling the fluidic transfer mechanism in between ones of the respective measurement cycles so as to expose the conductor surface to clean dry air.

7. The measurement method of claim 6, wherein the aqueous sample comprises water, and wherein the measurement method further comprises controlling an automated sample extraction mechanism, so as to intermittently draw water samples from a water supply.

8. The measurement method of claim 1, wherein measuring the analyte to detect the presence of the at least one metal substance comprises voltametrically measuring the at least one metal substance to obtain a result, and using at least one processor to calculate a concentration of the at least one metal substance responsive to said voltametrically measuring.

9. A voltametric measurement device, comprising:
   a measurement chamber;
   a fluidic transfer mechanism; and a working electrode, an auxiliary electrode and a reference electrode, wherein the reference electrode comprises a conductor surface having at least one of silver or silver chloride;

wherein for each of respective measurement cycles,
the fluidic transfer mechanism is to supply an analyte to the measurement chamber,
each of the working electrode, the auxiliary electrode and the reference electrode are to be immersed into the analyte within the measurement chamber, such that the conductor surface is placed in direct contact with the analyte,
the fluidic transfer mechanism is to add a source of chlorides to the analyte, to create a mixture,
the voltametric measurement device is to perform voltametric measurement of the mixture, to detect presence of a metal substance, and
following performance of voltametric measurement, the fluidic transfer mechanism is to automatically remove the mixture including the chlorides from the presence of the conductor surface; and
wherein the fluidic transfer mechanism is to, on an automated basis, clean the conductor surface in between ones of the respective measurement cycles by immersing the conductor surface in at least one of a fluoride-based substance or an add.

10. The voltametric measurement device of claim 9, wherein the voltametric measurement device is to expose the conductor surface to clean dry air in between ones of the respective measurement cycles.

11. The voltametric measurement device of claim 9, wherein the fluidic transfer mechanism is to, on an automated basis, immerse the conductor surface in a non-saline preservative in between ones of the respective measurement cycles.

12. The voltametric measurement device of claim 9, wherein the reference electrode comprises at least one of a silver wire or a silver chloride wire, and the voltametric measurement device is to immerse the at least one of the silver wire or the silver chloride wire directly into the analyte.

13. The voltametric measurement device of claim 9, further comprising an ultrasound transducer, wherein the voltametric measurement device is to, on an automated basis, clean the conductor surface in between ones of the respective measurement cycles by directing ultrasound energy from the ultrasound transducer toward the surface of the at least one of the electrodes, the directing being performed in the presence of the conductor surface.

14. The voltametric measurement device of claim 9, wherein each analyte is in the form of an aqueous sample, and wherein said voltametric measurement device comprises a control system to automatically initiate the respective measurement cycles on a calendared basis and to automatically control the fluidic transfer mechanism in between ones of the respective measurement cycles so as to expose the conductor surface to clean dry air.

15. The voltametric measurement device of claim 14, wherein the aqueous sample comprises water, and wherein the control system is to control an automated sample extraction mechanism, so as to intermittently draw water samples from a water supply.

16. A voltametric measurement device, comprising:
a measurement chamber;
a fluidic transfer mechanism; and
a working electrode, an auxiliary electrode and a reference electrode, wherein the reference electrode comprises a conductor surface having at least one of silver or silver chloride;
means for, for each of respective measurement cycles,
causing the fluidic transfer mechanism to supply an analyte to the measurement chamber, in a manner such that each of the working electrode, the auxiliary electrode and the reference electrode are immersed into the analyte within the measurement chamber, and such that the conductor surface is placed in direct contact with the analyte,
causing the fluidic transfer mechanism to add a source of chlorides to the analyte, to create a mixture,
performing voltametric measurement of the mixture, to detect presence of a metal substance, and
following performance of voltametric measurement, causing the fluidic transfer mechanism to automatically remove the mixture including the chlorides from the presence of the conductor surface;
wherein the voltametric measurement device further comprises means for, on an automated basis, causing the fluid transfer mechanism to clean the conductor surface in between ones of the respective measurement cycles by immersing the conductor surface in at least one of a fluoride-based substance or an add.

17. The voltametric measurement device of claim 16, further comprising means for measuring a condition of the reference electrode and for selectively initiating a cleaning cycle to clean the conductor surface dependent on the measured condition.

18. The voltametric measurement device of claim 16, wherein the voltametric measurement device further comprises means for, on an automated basis, cleaning the conductor surface in between ones of the respective measurement cycles by directing ultrasound energy toward the surface of the at least one of the electrodes, the directing being performed in the presence of the conductor surface.

19. The voltametric measurement device of claim 16, wherein each analyte is in the form of an aqueous sample, and wherein said means for cleaning further comprises means for automatically initiating the respective measurement cycles on a calendared basis and for automatically controlling the fluidic transfer mechanism in between ones of the respective measurement cycles so as to expose the conductor surface to clean dry air.

20. The voltametric measurement device of claim 19, wherein the aqueous sample comprises water, and wherein said means is further to control an automated sample extraction mechanism to intermittently draw water samples from a water supply.

* * * * *